United States Patent [19]
Roy et al.

[11] Patent Number: 5,589,363
[45] Date of Patent: Dec. 31, 1996

[54] DNA ENCODING TISSUE FACTOR MUTANTS USEFUL FOR THE TREATMENT OF MYOCARDIAL INFARCTION AND COAGULOPATHIC DISORDERS

[75] Inventors: Soumitra Roy, San Francisco; Gordon A. Vehar, San Carlos, both of Calif.

[73] Assignee: Genentech, Inc., South San Francisco, Calif.

[21] Appl. No.: 246,978

[22] Filed: May 20, 1994

Related U.S. Application Data

[62] Division of Ser. No. 714,819, Jun. 13, 1991, Pat. No. 5,346,991.
[51] Int. Cl.$^6$ .................. C07K 14/745; C12N 1/13; C12N 15/12; C12N 15/63
[52] U.S. Cl. .................. 435/69.6; 530/381; 536/23.5; 536/23.4; 435/172.3; 435/240.2; 435/252.3
[58] Field of Search .................. 435/69.6, 172.3, 435/252.3, 240.1, 320.1, 240.2; 530/350, 381; 536/23.5, 23.4

[56] References Cited

U.S. PATENT DOCUMENTS

| | | | |
|---|---|---|---|
| 4,966,852 | 10/1990 | Wun et al. | 435/320.1 |
| 5,110,730 | 5/1992 | Edgington | 435/69.6 |
| 5,374,617 | 12/1994 | Morrissey | 514/8 |

FOREIGN PATENT DOCUMENTS

| | | |
|---|---|---|
| 300988 | 1/1989 | European Pat. Off. . |
| 318451 | 5/1989 | European Pat. Off. . |
| WO89/09612 | 10/1989 | WIPO . |

OTHER PUBLICATIONS

Bach, "Initiation of Coagulation by Tissue Factor", *CRC Critical Reviews in Biochemistry*, 23(4):339–368 (1988).
Fisher et al., "Cloning and Expression of Human Tissue Factor cDNA", *Thrombosis Research*, 48:89–99 (1987).
Harrison's Principles of Internal Medicine, 11th Ed., p. 1478.
Krangel et al., "Characterization of a B Lymphoblastoid Cell Line Mutant that Secretes HLA–A2", *J. Immunol.*, 132(6):2984–2991 (1984).
Mason et al., "Activin B: Precursor Sequences, Genomic Structure and in Vitro Activities", *Molecular Endocrinology*, 3(9):1352–1358 (1989).
O'Brien et al., "Factor VIII–Bypassing Activity of Bovine Tissue Factor Using the Canine Hemophilic Model", *J. Clin. Invest.*, 82:206–211 (1988).
Paborsky et al., "Purification of Recombinant Human Tissue Factor", *Biochemistry*, 28(20):8072–8077 (1989).
Roy et al., "Self–association of Tissue Factor as Revealed by Chemical Cross–linking", *J. Biol. Chem.*, 266(8):4665–4668 (1991).
Sakai et al., "Binding of Human Factors VII and VIIa to a Human Bladder Carcinoma Cell Line (J82)", *J. Biol. Chem.*, 264(17):9980–9988 (1989).
Spicer et al., "Isolation of cDNA clones coding for human tissue factor: Primary structure of the protein and cDNA", *Proc. Natl. Acad. Sci. USA*, 84:5148–5152 (1987).
Taylor et al., "Lethal *E. coli* Septic Shock is Prevented by Blocking Tissue Factor With Monoclonal Antibody", *Circulatory Shock*, 33:127–134 (1991).

*Primary Examiner*—Dian C. Jacobson
*Attorney, Agent, or Firm*—Jeffrey S. Kubinec; Daryl B. Winter

[57] ABSTRACT

DNA enclosing a tissue factor protein mutant capable of neutralizing the ability of endogenous tissue factor to induce coagulation is provided. A representative tissue factor mutant designated K165A, K166A TF is useful in a method for inhibiting thrombin-induced platelet aggregation in a mammal, either separately or in combination with a thrombolytic agent, an anticoagulant, or a $GPII_{bIIIa}$ inhibitor.

16 Claims, 8 Drawing Sheets

CCCTCGCACT CCCTCTGGCC GGCCCAGGGC GCCTTCAGCC CAACCTCCCC 50

AGCCCCACGG GCGCCACGGA ACCCGCTCGA TCTCGCCGCC AACTGGTAGA 100

```
C   ATG GAG ACC CCT GCC TGG CCC CGG GTC CCG CGC CCC 137
    Met Glu Thr Pro Ala Trp Pro Arg Val Pro Arg Pro
    -32     -30             -25

GAG ACC GCC GTC GCT CGG ACG CTC CTG CTC GGC TGG GTC 176
Glu Thr Ala Val Ala Arg Thr Leu Leu Leu Gly Trp Val
-20             -15                 -10

TTC GCC CAG GTG GCC GGC GCT TCA GGC ACT ACA AAT ACT 215
Phe Ala Gln Val Ala Gly Ala Ser Gly Thr Thr Asn Thr
            -5              1               5

GTG GCA GCA TAT AAT TTA ACT TGG AAA TCA ACT AAT TTC 254
Val Ala Ala Tyr Asn Leu Thr Trp Lys Ser Thr Asn Phe
                10              15

AAG ACA ATT TTG GAG TGG GAA CCC AAA CCC GTC AAT CAA 293
Lys Thr Ile Leu Glu Trp Glu Pro Lys Pro Val Asn Gln
20              25                  30

GTC TAC ACT GTT CAA ATA AGC ACT AAG TCA GGA GAT TGG 332
Val Tyr Thr Val Gln Ile Ser Thr Lys Ser Gly Asp Trp
        35              40                      45

AAA AGC AAA TGC TTT TAC ACA ACA GAC ACA GAG TGT GAC 371
Lys Ser Lys Cys Phe Tyr Thr Thr Asp Thr Glu Cys Asp
                50              55

CTC ACC GAC GAG ATT GTG AAG GAT GTG AAG CAG ACG TAC 410
Leu Thr Asp Glu Ile Val Lys Asp Val Lys Gln Thr Tyr
        60              65              70

TTG GCA CGG GTC TTC TCC TAC CCG GCA GGG AAT GTG GAG 449
Leu Ala Arg Val Phe Ser Tyr Pro Ala Gly Asn Val Glu
            75              80

AGC ACC GGT TCT GCT GGG GAG CCT CTG TAT GAG AAC TCC 488
Ser Thr Gly Ser Ala Gly Glu Pro Leu Tyr Glu Asn Ser
85              90                  95

CCA GAG TTC ACA CCT TAC CTG GAG ACA AAC CTC GGA CAG 527
Pro Glu Phe Thr Pro Tyr Leu Glu Thr Asn Leu Gly Gln
        100             105                 110
```

FIG. IA

| | | | | | | | | | | | | |
|---|---|---|---|---|---|---|---|---|---|---|---|---|
| CCA | ACA | ATT | CAG | AGT | TTT | GAA | CAG | GTG | GGA | ACA | AAA | GTG 566 |
| Pro | Thr | Ile | Gln | Ser<br>115 | Phe | Glu | Gln | Val | Gly<br>120 | Thr | Lys | Val |

```
CCA ACA ATT CAG AGT TTT GAA CAG GTG GGA ACA AAA GTG  566
Pro Thr Ile Gln Ser Phe Glu Gln Val Gly Thr Lys Val
            115             120

AAT GTG ACC GTA GAA GAT GAA CGG ACT TTA GTC AGA AGG  605
Asn Val Thr Val Glu Asp Glu Arg Thr Leu Val Arg Arg
    125             130             135

AAC AAC ACT TTC CTA AGC CTC CGG GAT GTT TTT GGC AAG  644
Asn Asn Thr Phe Leu Ser Leu Arg Asp Val Phe Gly Lys
            140             145

GAC TTA ATT TAT ACA CTT TAT TAT TGG AAA TCT TCA AGT  683
Asp Leu Ile Tyr Thr Leu Tyr Tyr Trp Lys Ser Ser Ser
150             155             160

TCA GGA GCG GCA ACA GCC AAA ACA AAC ACT AAT GAG TTT  722
Ser Gly Ala Ala Thr Ala Lys Thr Asn Thr Asn Glu Phe
            165             170             175

TTG ATT GAT GTG GAT AAA GGA GAA AAC TAC TGT TTC AGT  761
Leu Ile Asp Val Asp Lys Gly Glu Asn Tyr Cys Phe Ser
                180             185

GTT CAA GCA GTG ATT CCC TCC CGA ACA GTT AAC CGG AAG  800
Val Gln Ala Val Ile Pro Ser Arg Thr Val Asn Arg Lys
            190             195             200

AGT ACA GAC AGC CCG GTA GAG TGT ATG GGC CAG GAG AAA  839
Ser Thr Asp Ser Pro Val Glu Cys Met Gly Gln Glu Lys
                205             210

GGG GAA TTC AGA GAA ATA TTC TAC ATC ATT GGA GCT GTG  878
Gly Glu Phe Arg Glu Ile Phe Tyr Ile Ile Gly Ala Val
215             220             225

GTA TTT GTG GTC ATC ATC CTT GTC ATC ATC CTG GCT ATA  917
Val Phe Val Val Ile Ile Leu Val Ile Ile Leu Ala Ile
            230             235             240

TCT CTA CAC AAG TGT AGA AAG GCA GGA GTG GGG CAG AGC  956
Ser Leu His Lys Cys Arg Lys Ala Gly Val Gly Gln Ser
                245             250

TGG AAG GAG AAC TCC CCA CTG AAT GTT TCA TAAA  990
Trp Lys Glu Asn Ser Pro Leu Asn Val Ser
255             260         263
```

FIG. IB

```
GGAAGCACTG TTGGAGCTAC TGCAAATGCT ATATTGCACT GTGACCGAGA 1040

ACTTTTAAGA GGATAGAATA CATGGAAACG CAAATGAGTA TTTCGGAGCA 1090

TGAAGACCCT GGAGTTCAAA AAACTCTTGA TATGACCTGT TATTACCATT 1140

AGCATTCTGG TTTTGACATC AGCATTAGTC ACTTTGAAAT GTAACGAATG 1190

GTACTACAAC CAATTCCAAG TTTTAATTTT TAACACCATG GCACCTTTTG 1240

CACATAACAT GCTTTAGATT ATATATTCCG CACTCAAGGA GTAACCAGGT 1290

CGTCCAAGCA AAAACAAATG GGAAAATGTC TTAAAAAATC CTGGGTGGAC 1340

TTTTGAAAAG CT 1352
```

FIG. IC

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1352 nucleotides
        ( B ) TYPE: Nucleic Acid
        ( C ) STRANDEDNESS: Double
        ( D ) TOPOLOGY: Linear ( x i ) SEQUENCE DESCRIPTION: SEQ ID NO:1:

```
CCCTCGCACT   CCCTCTGGCC   GGCCCAGGGC   GCCTTCAGCC   CAACCTCCCC                    50

AGCCCCACGG   GCGCCACGGA   ACCCGCTCGA   TCTCGCCGCC   AACTGGTAGA                   100

C     ATG   GAG   ACC   CCT   GCC   TGG   CCC   CGG   GTC   CCG   CGC   CCC      137
      Met   Glu   Thr   Pro   Ala   Trp   Pro   Arg   Val   Pro   Arg   Pro
      -32         -30                           -25

GAG   ACC   GCC   GTC   GCT   CGG   ACG   CTC   CTG   CTC   GGC   TGG   GTC      176
Glu   Thr   Ala   Val   Ala   Arg   Thr   Leu   Leu   Leu   Gly   Trp   Val
-20                     -15                           -10

TTC   GCC   CAG   GTG   GCC   GGC   GCT   TCA   GGC   ACT   ACA   AAT   ACT      215
Phe   Ala   Gln   Val   Ala   Gly   Ala   Ser   Gly   Thr   Thr   Asn   Thr
            -5                            1                     5

GTG   GCA   GCA   TAT   AAT   TTA   ACT   TGG   AAA   TCA   ACT   AAT   TTC      254
Val   Ala   Ala   Tyr   Asn   Leu   Thr   Trp   Lys   Ser   Thr   Asn   Phe
                  10                        15

AAG   ACA   ATT   TTG   GAG   TGG   GAA   CCC   AAA   CCC   GTC   AAT   CAA      293
Lys   Thr   Ile   Leu   Glu   Trp   Glu   Pro   Lys   Pro   Val   Asn   Gln
20                      25                        30

GTC   TAC   ACT   GTT   CAA   ATA   AGC   ACT   AAG   TCA   GGA   GAT   TGG      332
Val   Tyr   Thr   Val   Gln   Ile   Ser   Thr   Lys   Ser   Gly   Asp   Trp
            35                        40                        45

AAA   AGC   AAA   TGC   TTT   TAC   ACA   ACA   GAC   ACA   GAG   TGT   GAC      371
Lys   Ser   Lys   Cys   Phe   Tyr   Thr   Thr   Asp   Thr   Glu   Cys   Asp
                  50                        55

CTC   ACC   GAC   GAG   ATT   GTG   AAG   GAT   GTG   AAG   CAG   ACG   TAC      410
Leu   Thr   Asp   Glu   Ile   Val   Lys   Asp   Val   Lys   Gln   Thr   Tyr
      60                        65                        70

TTG   GCA   CGG   GTC   TTC   TCC   TAC   CCG   GCA   GGG   AAT   GTG   GAG      449
Leu   Ala   Arg   Val   Phe   Ser   Tyr   Pro   Ala   Gly   Asn   Val   Glu
            75                        80

AGC   ACC   GGT   TCT   GCT   GGG   GAG   CCT   CTG   TAT   GAG   AAC   TCC      488
Ser   Thr   Gly   Ser   Ala   Gly   Glu   Pro   Leu   Tyr   Glu   Asn   Ser
85                        90                        95

CCA   GAG   TTC   ACA   CCT   TAC   CTG   GAG   ACA   AAC   CTC   GGA   CAG      527
```

|  |  |
|---|---:|
| Pro Glu Phe Thr Pro Tyr Leu Glu Thr Asn Leu Gly Gln<br>　　　　100　　　　　　　　　105　　　　　　　　　110 |  |
| CCA ACA ATT CAG AGT TTT GAA CAG GTG GGA ACA AAA GTG<br>Pro Thr Ile Gln Ser Phe Glu Gln Val Gly Thr Lys Val<br>　　　　　　　　115　　　　　　　　　120 | 566 |
| AAT GTG ACC GTA GAA GAT GAA CGG ACT TTA GTC AGA AGG<br>Asn Val Thr Val Glu Asp Glu Arg Thr Leu Val Arg Arg<br>　　　　125　　　　　　　　　130　　　　　　　　　135 | 605 |
| AAC AAC ACT TTC CTA AGC CTC CGG GAT GTT TTT GGC AAG<br>Asn Asn Thr Phe Leu Ser Leu Arg Asp Val Phe Gly Lys<br>　　　　　　　　140　　　　　　　　　145 | 644 |
| GAC TTA ATT TAT ACA CTT TAT TAT TGG AAA TCT TCA AGT<br>Asp Leu Ile Tyr Thr Leu Tyr Tyr Trp Lys Ser Ser Ser<br>150　　　　　　　　　155　　　　　　　　　160 | 683 |
| TCA GGA GCG GCA ACA GCC AAA ACA AAC ACT AAT GAG TTT<br>Ser Gly Ala Ala Thr Ala Lys Thr Asn Thr Asn Glu Phe<br>　　　　165　　　　　　　　　170　　　　　　　　　175 | 722 |
| TTG ATT GAT GTG GAT AAA GGA GAA AAC TAC TGT TTC AGT<br>Leu Ile Asp Val Asp Lys Gly Glu Asn Tyr Cys Phe Ser<br>　　　　　　　　180　　　　　　　　　185 | 761 |
| GTT CAA GCA GTG ATT CCC TCC CGA ACA GTT AAC CGG AAG<br>Val Gln Ala Val Ile Pro Ser Arg Thr Val Asn Arg Lys<br>　　　　190　　　　　　　　　195　　　　　　　　　200 | 800 |
| AGT ACA GAC AGC CCG GTA GAG TGT ATG GGC CAG GAG AAA<br>Ser Thr Asp Ser Pro Val Glu Cys Met Gly Gln Glu Lys<br>　　　　　　　　205　　　　　　　　　210 | 839 |
| GGG GAA TTC AGA GAA ATA TTC TAC ATC ATT GGA GCT GTG<br>Gly Glu Phe Arg Glu Ile Phe Tyr Ile Ile Gly Ala Val<br>215　　　　　　　　　220　　　　　　　　　225 | 878 |
| GTA TTT GTG GTC ATC ATC CTT GTC ATC ATC CTG GCT ATA<br>Val Phe Val Val Ile Ile Leu Val Ile Ile Leu Ala Ile<br>　　　　230　　　　　　　　　235　　　　　　　　　240 | 917 |
| TCT CTA CAC AAG TGT AGA AAG GCA GGA GTG GGG CAG AGC<br>Ser Leu His Lys Cys Arg Lys Ala Gly Val Gly Gln Ser<br>　　　　　　　　245　　　　　　　　　250 | 956 |
| TGG AAG GAG AAC TCC CCA CTG AAT GTT TCA TAA AGG AAG<br>Trp Lys Glu Asn Ser Pro Leu Asn Val Ser Xaa Arg Lys<br>255　　　　　　　　　260　　　　　　　　　265 | 995 |
| CAC TGT TGG AGC TAC TGC AAA TGC TAT ATT GCA CTG TGA<br>His Cys Trp Ser Tyr Cys Lys Cys Tyr Ile Ala Leu Xaa<br>　　　　270　　　　　　　　　275 | 1034 |
| CCG AGA ACT TTT AAG AGG ATA GAA TAC ATG GAA ACG CAA<br>Pro Arg Thr Phe Lys Arg Ile Glu Tyr Met Glu Thr Gln<br>280　　　　　　　　　285　　　　　　　　　290 | 1073 |
| ATG AGT ATT TCG GAG CAT GAA GAC CCT GGA GTT CAA AAA<br>Met Ser Ile Ser Glu His Glu Asp Pro Gly Val Gln Lys<br>　　　　295　　　　　　　　　300　　　　　　　　　305 | 1112 |
| ACT CTT GAT ATG ACC TGT TAT TAC CAT TAG CAT TCT GGT<br>Thr Leu Asp Met Thr Cys Tyr Tyr His Xaa His Ser Gly<br>　　　　　　　　310　　　　　　　　　315 | 1151 |
| TTT GAC ATC AGC ATT AGT CAC TTT GAA ATG TAA CGA ATG<br>Phe Asp Ile Ser Ile Ser His Phe Glu Met Xaa Arg Met<br>320　　　　　　　　　325　　　　　　　　　330 | 1190 |
| GTA CTA CAA CCA ATT CCA AGT TTT AAT TTT TAA CAC CAT<br>Val Leu Gln Pro Ile Pro Ser Phe Asn Phe Xaa His His<br>　　　　335　　　　　　　　　340 | 1229 |
| GGC ACC TTT TGC ACA TAA CAT GCT TTA GAT TAT ATA TTC<br>Gly Thr Phe Cys Thr Xaa His Ala Leu Asp Tyr Ile Phe<br>345　　　　　　　　　350　　　　　　　　　355 | 1268 |
| CGC ACT CAA GGA GTA ACC AGG TCG TCC AAG CAA AAA CAA | 1307 |

```
Arg  Thr  Gln  Gly  Val  Thr  Arg  Ser  Ser  Lys  Gln  Lys  Gln
          360                      365                370

ATG  GGA  AAA  TGT  CTT  AAA  AAA  TCC  TGG  GTG  GAC  TTT  TGA                1346
Met  Gly  Lys  Cys  Leu  Lys  Lys  Ser  Trp  Val  Asp  Phe  Xaa
               375                      380

AAA  GCT                                                                        1352
Lys  Ala
     385
```

( 2 ) INFORMATION FOR SEQ ID NO:2:

( i ) SEQUENCE CHARACTERISTICS:
        ( A ) LENGTH: 30 nucleotides
        ( B ) TYPE: Nucleic Acid
        ( C ) STRANDEDNESS: Single
        ( D ) TOPOLOGY: Linear ( x i ) SEQUENCE DESCRIPTION: SEQ ID NO:2:

TCAAGTTCAG GAGCGGCAAC AGCCAAAACA                                                30

( 2 ) INFORMATION FOR SEQ ID NO:3:

( i ) SEQUENCE CHARACTERISTICS:
        ( A ) LENGTH: 17 nucleotides
        ( B ) TYPE: Nucleic Acid
        ( C ) STRANDEDNESS: Single
        ( D ) TOPOLOGY: Linear ( x i ) SEQUENCE DESCRIPTION: SEQ ID NO:3:

CAACACTTTC CTAAGCC                                                              17

DNA ENCODING TISSUE FACTOR MUTANTS USEFUL FOR THE TREATMENT OF MYOCARDIAL INFARCTION AND COAGULOPATHIC DISORDERS

CROSS REFERENCES

This application is a divisional of earlier filed U.S. application Ser. No. 07/714,819 filed Jun. 13, 1991, U.S. Pat. No. 5,346,991, which application is incorporated herein by reference and to which application we claim priority under 35 USC §120.

FIELD OF THE INVENTION

This invention relates to the treatment of myocardial infarction and more particularly to a therapy for preventing the reocclusion of coronary arteries which often accompanies use of thrombolytic agents in the treatment of myocardial infarction. This invention also relates to the treatment of coagulopathic disorders such as septic shock where overexpression of endogenous tissue factor may lead to disseminated intravascular coagulation (DIC). This invention further relates to the use of tissue factor protein mutants to prevent reocclusion of a coronary artery or to treat DIC and septic shock.

BACKGROUND OF THE INVENTION

The initiating event of many myocardial infarctions (heart attacks) is hemorrhage into an atherosclerotic plaque. Such hemorrhage may result in formation of a thrombus or blood clot in the coronary artery which supplies the infarct zone (i.e., an area of necrosis which results from an obstruction of blood circulation). This thrombus is composed of a combination of fibrin and blood platelets. The formation of a fibrin-platelet clot has sedous clinical ramifications. The degree and duration of the occlusion caused by the fibrin-platelet clot determines the mass of the infarct zone and the extent of damage.

The goal of current treatment for myocardial infarction is the rapid dissolution of the occluding thrombus (thrombolysis) and the restoration of normal blood flow (reperfusion). Successful therapy should include elimination of the fibrin-platelet clot and prevention of its reformation. If the fibrin-platelet clot reforms, then the affected artery may become reoccluded, reversing the benefits of thrombolytic therapy.

The formation of fibrin-platelet clots in other parts of the circulatory system may be partially prevented through the use of anti-coagulants such as heparin. Unfortunately, heparin therapy has not been found to be universally effective in preventing reocclusion in myocardial infarction victims where the degree of blood vessel occlusion (the degree of stenosis) is greater than or equal to about 70%, especially in those patients with severe residual coronary stenosis.

If an individual has formed a fibdn-platelet clot, the clot may be dissolved through the use of a thrombolytic agent. A thrombolytic agent is a medicament capable of lysing the fibrin-platelet thrombus, and thereby permitting blood to again flow through the affected blood vessel. Such agents include; streptokinase, streptokinaseanalogues, prourokinase, urokinase, and tissue-type plasminogen activator (t-PA) (Ganz, W. et al., *J. Amer. Coll. Cardiol.* 1:1247–1253 [1983]; Rentrop, K. P. et al., *Amer. J. Cardiol.*, 54:29E–31E [1984]; Gold, H. K. et al., *Amer. J. Cardiol.*, 53:22C–125C [1984]).

Treatment with thrombolytic agents can often successfully restore coronary blood flow rapidly enough to interrupt myocardial infarction. Unfortunately, the dissolved fibdn-platelet clot has been found in a number of patients to reform after cessation of such thrombolytic therapy. This reformation may result in the reocclusion of the affected blood vessels, and is, therefore, of substantial concern (Gold, H. K. et al., supra; Gold H. K. et al., *Circulation*, 68:150–154 [1983]). Thus, although streptokinase treatment has been found to be successful in dissolving fibrin clots, reocclusion of the affected vessels has been found to occur in approximately 25% of the patients examined (Gold, H. K., et al., *Circulation* 68:150–154 [1983]).

Tissue-type plasminogen activator is believed to be a more desirable thrombolytic agent than either streptokinase or urokinase because it displays greater (though not absolute) specificity for fibrin than either of these latter agents (Verstrate, M., et al., *Lancet* 1:142 [1985]). Tissue-type plasminogen activator t-PA also displays a rapid clearing rate from plasma. t-PA has been found to be an effective thrombolytic agent in patients with acute myocardial infarction, producing coronary reflow (i.e., decreasing stenosis) in 45–75 minutes in approximately 70% of patients studied (Gold, H. K. et al., *Circulation* 73:347–352 [1986]).

Typically, tissue-type plasminogen activator is administered as an infusion at a rate of approximately 100 mg/patient. The benefit of employing t-PA is significantly offset by the spontaneous rate of acute reocclusion which follows the cessation of t-PA therapy. It has been observed that cessation of t-PA therapy resulted in reocclusion of affected blood vessels in approximately 45% of patients studied (*Circulation* 73:347–352 [1986]). Increased t-PA dosages have not been found to decrease the tendency for coronary artery reocclusion. Significantly, the possibility of thrombin clot reformation is closely related to the degree of residual coronary stenosis (i.e., the extent of blood vessel blockage). Thus, reocclusion is more probable in individuals in which high grade stenosis (i.e., greater than 70% quantitative stenosis or greater than 80% non-quantitative stenosis) has occurred. The reocclusion of blood vessels has been found to be inhibited by continued infusion of t-PA (Gold, H. K. et al., *Circulation* 73:347–352 [1986]).

The general mechanism of blood clot formation is reviewed by Ganong, W. F. (In: *Review of Medical Physiology*, 13th ed., Lange, Los Altos, Calif., pp 411–414 [1987]). Blood coagulation requires the confluence of two processes; the production of thrombin which induces platelet aggregation and the formation of fibrin which renders the platelet plug stable. A number of discrete proenzymes and procofactors, referred to as coagulation factors, participate in the coagulation process. The process comprises several stages, each requiring separate coagulation factor and ends in fibrin cross-linking and thrombus formation. Briefly, fibrinogen is converted to fibrin by the action of thrombin. Thrombin, in turn, is formed by the proteolytic cleavage of a proenzyme, prothrombin. This proteolysis is effected by activated factor X (factor $X_a$) which binds to the surface of activated platelets and, in the presence of factor $V_a$ and calcium ion cleaves prothrombin.

Activation of factor X may occur by either of two separate pathways, referred to as the extrinsic and intrinsic pathways. The intrinsic pathway or cascade consists of a series of reactions in which a protein precursor is cleaved to form an active protease. At each stage, the newly formed protease will catalyze the activation of another protease used in a subsequent step of the cascade. Thus the protein product (active protease) of each step acts as a catalyst for the next step. Such a cascade results in a significant amplification of the thrombus forming. A deficiency of any of the proteins in the cascade blocks the activation process at that step, thereby inhibiting or preventing clot formation. Deficiencies of factor VIII or factor IX, for example, are known to cause the bleeding syndromes haemophilia A and B, respectively. In the extrinsic pathway of blood coagulation, tissue factor, also referred to as tissue thromboplastin, is released from damaged cells and facilitates factor X activation in the presence of factor VII and calcium. Although activation of factor X was originally believed to be the only reaction catalyzed by tissue factor and factor VII, it is now known that an amplification loop exists between factor X, factor VII, and factor IX (Osterud, B., and S. I. Rapaport, *Proc. Natl. Acad. Sci. USA* 74:5260–5264, 1977 and Zur, M. et al., *Blood* 52:198, [1978]). Each of the sedne proteases in this scheme is capable of converting, by proteolysis, the other two into the activated form, thereby amplifying the signal at this stage in the coagulation process. It is now believed that the extrinsic pathway may in fact be the major physiological pathway of normal blood coagulation (*Haemostasis* 13:150–155 [1983]). Since tissue factor is not normally found in the blood, the system does not continuously clot; the trigger for coagulation would therefore be the release or exposure of tissue factor from damaged tissue, e.g. atherosclerotic plaque.

Tissue factor is an integral membrane glycoprotein which, as discussed above, can trigger blood coagulation via the extrinsic pathway. (Bach, R. et al., *J. Biol Chem.* 256(16): 8324–8331 [1981]). Tissue factor consists of a protein component (previously referred to as tissue factor apoprotein-III) and a phospholipid. (Osterud, B. and Rapaport, S. I., *PNAS,* 74:5260–5264 [1977]). The complex has been found on the membranes of monocytes and other cells of the blood vessel wall. (Osterud, B., Scand. *J. Haematol.* 32:337–345 [1984]). Recent characterization of tissue factor protein reveals the protein to have a molecular weight of approximately 30,000 daltons. Three aspargimine-linked carbohydrate structures increase the apparent molecular weight (SDS-PAGE) to about 45,000 daltons (Bach, R. CRC. *Crit. Rev. Biochem.*, 23:339–368 [1988]). Human tissue thromboplastin has been described as consisting of a tissue factor protein inserted into phospholipid bilayer in an optimal ratio of tissue factor protein: phospholipid of approximately 1:80 (Lyberg, T. and Prydz, H., *Nouv. Rev. Fr. Hematol.* 25(5):291–293 [1983]). Purification of tissue factor has been reported from various tissues such as human brain (Guha, A. et al. *PNAS* 83:299–302 [1986] and Broze, G. H. et al., *J. Biol. Chem.* 260:10917–10920 [1985]), bovine brain (Bach, R. et al., *J. Biol. Chem.* 256:8324–8331 [1981]), human placenta (Born, V. J. J. et al., i Thrombosis Res. 42:635–643 [1986], and, Andoh, K. et al., *Thrombosis Res.* 43:275–286 [1986]), ovine brain (Carlsen, E. et al., *Thromb. Haemostas.* 48(3):315–319 [1982]), and lung (Glas, P. and Astrup, T., *Am. J. Physiol.,* 219:1140–1146 [1970]). It has been shown that bovine and human tissue thromboplastin are identical in size and function. (See for example Broze, G., et al., *J. Biol. Chem.* 260(20):10917–10920 [1985]). It is widely accepted that while there are differences in structure of tissue factor protein between species there are no functional differences as measured by in vitro coagulation assays. Furthermore, tissue factor isolated from various tissues of an animal, e.g. dog brain, lung, arteries and vein has been shown to be similar in certain respects such as, extinction coefficient, content of nitrogen and phosphorous and optimum phospholipid to lipid ratio but different slightly in molecular size, amino acid content, reactivity with antibody and plasma half life (Gonmori, H. and Takeda, Y., *J. Physiol.* 229(3):618–626 [1975]). It is also widely accepted that in order to demonstrate biological activity, tissue factor must be associated with phospholipids (Pitlick, F. A. et al., *Biochemistry* 9:5105–5111 [1970] and Bach, R. et al. supra. at 8324). It has been shown that the removal of the phospholipid component of tissue factor, for example by use of a phospholipase, results in a loss of its biological activity (Nemerson, Y., J. C. I. 47:72–80 [1968]). Relipidation can restore in vitro tissue factor activity. Pitlick, F. A. supra, and Freyssinet, J. M. et al., *Thrombosis and Haemostasis* 55:112–118 [1986]).

Infusion of tissue factor has long been believed to compromise normal haemostasis. In 1834 the French physiologist de Blainville first established that tissue factor contributed directly to blood coagulation (de Blainville, H. Gazette Medicale Paris, *Series* 2, 524 [1834]). de Blainville also observed that intravenous infusion of a brain tissue suspension caused immediate death which he observed was correlated with a hypercoagulative state giving rise to extensively disseminated blood clots found on autopsy. It is now well accepted that intravenous infusion of tissue thromboplastin induces intravascular coagulation and may cause death in various animals (dogs: Lewis, J. and Szeto I. F., *J. Lab. Clin. Med.* 60:261–273 (1962); rabbits: Fedder, G. et al., *Thromb. Diath. Haemorrh.* 27:365–376 (1972); rats: Giercksky, K. E. et al., *Scand. J. Haematol.* 17:305–311 (1976); and, sheep: Carlsen, E. et al., *Thromb. Haemostas.* 48:315–319 [1982]).

In addition to intravascular coagulation or a hypercoagulative state resulting from the exogenous administration of tissue factor, it has been suggested that the intravascular release of tissue thromboplastin may initiate a coagulopathic response such as disseminated intravascular coagulation (DIC) (Prentice, C. R., *Clin. Haematol.* 14(2):413–442 [1985]). DIC may arise in various conditions such as shock, septicaemia, cardiac arrest, extensive trauma, bites of poisonous snakes, acute liver disease, major surgery, burns, septic abortion, heat stroke, disseminated malignancy, pancreatic and ovarian carcinoma, promyelocytic leukemia, myocardial infarction, neoplasms, systemic lupus erythematosus, renal disease and eclampsia. Thus, the coagulopathic response is known to be associated with vadous disease states including but not limited to septic shock. How the coagulopathic state is induced during septic shock is not known with certainty, but it probably involves alterations in procoagulant, anticoagulant, and/or fibdnolytic properties of endothelial cells as well as other cells within the vasculature (Taylor et al., *Circulatory Shock* 33:127–134 [1991]). The cause of septic shock can not always be determined, however, it is frequently associated with gram-negative bacterial infection. Gram-negative bacteremia poses a major health problem, causing one-half of cases of lethal septic shock acquired during hospitalization. Bacterial lipopolysaccharide (LPS) and the inflammatory cytokines; tumor necrosis factor (TNF); and interleukin-1 (IL-1), have been shown to be essential mediators of septic shock. Among the effects of these mediators is a coagulopathy that may be triggered by induced expression of tissue factor (TF) on macrophages and endothelial cells. As described above, tissue factor is known to be a potent initiator of the coagulation cascade. Lipopolysaccharide (LPS) from *E. coli* can both directly and indirectly induce monocytes and macrophages to express TF, as well as to secrete inflammatory cytokines, such as interleukin-1 (IL-1) and tumor necrosis factor a (TNFα)(Old, Science, 8:630–632 [1985]). LPS can also induce TF in endothelial cells (Colucci et al., *J. Clin. Invest.,* 71:1893–1896 [1983]). IL-1 and TNFα, which are major mediators of shock in gram-negative sepsis (Tracey et al., *Nature* (London), 330:662–664 [1984]) in turn can induce expression of TF by endothelial cells cultured in vitro. It is therefore probable that induced expression of TF of monocytes/macrophages and endothelial cells is responsible for triggering the coagulation cascade during septic shock. Present treatment of DIC includes transfusion of blood and fresh frozen plasma; infusion of hepadn; and removal of formed thrombi.

The foregoing clinical syndromes suggest that endogenous release of tissue factor can result in severe clinical complications (see also Andoh, K. et al., *Thromb. Res.*, 43:275–286 [1986]). Efforts have been made to overcome the thrombotic effect of tissue thromboplastin using the enzyme thromboplastinase and a monoclonal antibody specific for tissue factor. Thromboplastinase is a phospholipase and would presumably cleave the phospholipid portion of tissue factor (Gollub, S. et al., *Thromb. Diath. Haemorh.* 7:470–479 [1962]). Immunoglobulin G (IgG) or Fab fragments of a monoclonal antibody against tissue factor administered to baboons as a pretreatment has recently been shown to attenuate coagulopathy and protect against an otherwise lethal dose of *E coli*. (Taylor, supra).

None of the foregoing references suggest a form of tissue factor protein capable of neutralizing the effect of endogenous TF to prevent or inhibit coagulation. A need for such a protein exists since it would provide an important adjunct to thrombolytic therapy as well as neutralize the hypercoagulative effects of induced or endogenously produced TF.

An object of the present invention is to provide an effective therapy for myocardial infarction which limits necrosis by permitting early reperfusion and by preventing reocclusion.

A further object of this invention is to provide a therapeutic composition for treatment of myocardial infarction and prevention of reformation of fibrin-platelet clots, i.e. reocclusion.

Yet another object of this invention is to provide an anticoagulant therapeutic, that is an antagonist to tissue factor protein, to neutralize the thrombotic effects of endogenous release of tissue thromboplastin which may result in a hypercoagulative state. Particularly, such an anticoagulant, that is an antagonist to tissue factor protein, would neutralize the hypercoagulant effects of endogenously released tissue thromboplastin by competing with tissue factor protein binding to factor VII.

SUMMARY OF THE INVENTION

The objects of this invention are achieved by providing a tissue factor protein mutant capable of neutralizing the ability of wild type or endogenous tissue factor to induce coagulation. Preferably, the tissue factor protein mutant of this invention will have at least 75% homology with a peptide selected from either; mature human tissue factor protein mutant of FIG. 1 (SEQ ID NO: 1), mature human tissue factor protein mutant of FIG. 1 (SEQ ID NO: 1) having the cytoplasmic domain deleted (e.g., deletion of amino acid residues 243–263), or soluble human tissue factor protein mutant of FIG. 1 (SEQ ID NO: 1) having the both the cytoplasmic domain and transmembrane domain deleted (e.g., amino acid residues from about 220–263 deleted). The tissue factor protein mutant of this invention preferably has the positively charged amino acid residues 165 and 166 substituted with an amino acid other than one bearing a positively charged sidechain at physiological pH.

Typically, amino acid residues 165 and 166 will be any $\alpha$-amino acid other than lysine or arginine, preferably those $\alpha$-amino acids will be selected from amino acids bearing an uncharged side chain, and most preferably, the $\alpha$-amino acids will be alanine. Optionally, one or both positively charged amino acid residue 165 and 166 are substituted with a negatively charged amino acid residue, preferably aspartic or glutamic acid. In the case where the tissue factor protein mutant contains alanine at both amino acid residue 165 and 166, the mutant will also preferably have amino acid residues 243–263 deleted. Optionally, the foregoing double alanine mutant will be the soluble form having amino acid residues 220–263 deleted. Also optionally, the tissue factor protein mutant may be fused to a heterologous polypeptide.

The instant invention includes a nucleic acid molecule encoding a tissue factor protein mutant capable of neutralizing the ability of endogenous or wild type tissue factor to induce coagulation. Optionally, the nucleic acid molecule will be operably linked to a promoter. Preferably, the nucleic acid molecule will be contained in an expression vector operably linked to control sequences recognized by a host cell transformed with the vector. The invention further encompasses a host cell transformed with the foregoing vector.

The invention also further contemplates a method of making a tissue factor protein mutant capable of neutralizing the ability of endogenous tissue factor to induce blood coagulation. This method includes expressing the tissue factor protein mutant in a cultured host cell transformed with a vector comprising the nucleic acid molecule encoding the tissue factor protein mutant operably linked to control sequences recognized by the host cell transformed with the vector, and recovering the tissue factor protein mutant from the host cell. Optionally, the tissue factor protein mutant is recovered from the host cell culture medium.

The invention includes a pharmaceutical composition containing the instant tissue factor protein mutant in admixture with a pharmaceutically acceptable carrier. This pharmaceutical composition is employed in a method for inhibiting thrombin-induced platelet aggregation in a mammal and consists of administering a pharmaceutically effective amount of the therapeutic composition to the mammal. Typically, the mammal treated will have an increased propensity for thrombus formation. Optionally, the instant therapeutic composition will be administered in combination with a thrombolytic agent, especially t-PA, or an anticoagulant such as hirudin, hirudin analogues, heparin, and Argatroban, or in combination with a $GPII_bIII_a$ inhibitor, especially those containing the recognition sequences; Arg-Gly-Asp, and Lys-Gly-Asp.

The invention further includes a kit containing the tissue factor protein mutant capable of neutralizing the ability of endogenous tissue factor to induce coagulation in combination with one or more additional therapeutic agents in colluding a thrombolytic agent, an anti-coagulant, or a $GPII_bIII_a$ inhibitor.

BRIEF DESCRIPTION OF THE DRAWINGS

FIG. 1 FIGS. 1A, 1B, and 1C are collectively referred to throughout the specification including the claims as FIG. 1 (SEQ ID NO: 1). Nucleotide and amino acid sequence of a tissue factor protein mutant capable of neutralizing the ability of endogenous tissue factor to induce coagulation.

Figure 2:
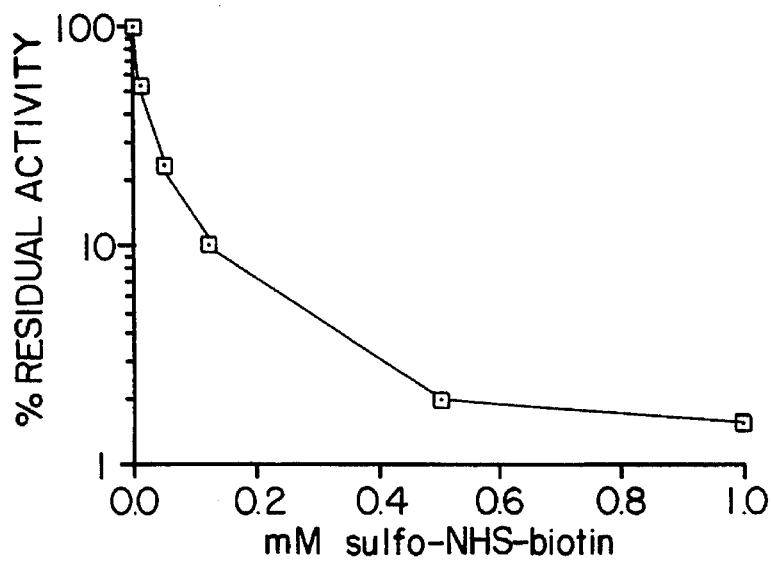
FIG. 2 Inactivation of tissue factor by sulfo-NHS-biotin. Recombinant human tissue factor lacking the cytoplasmic domain and expressed and purified from *E. coli* at a concentration of 500 ng/ml was treated with different concentrations of sulfo-NHS-biotin at room temperature for two hours and assayed for activity as described in O'Brien et al., *J. Clin. Invest*, 82:206–211 (1988).
Figure 3A:
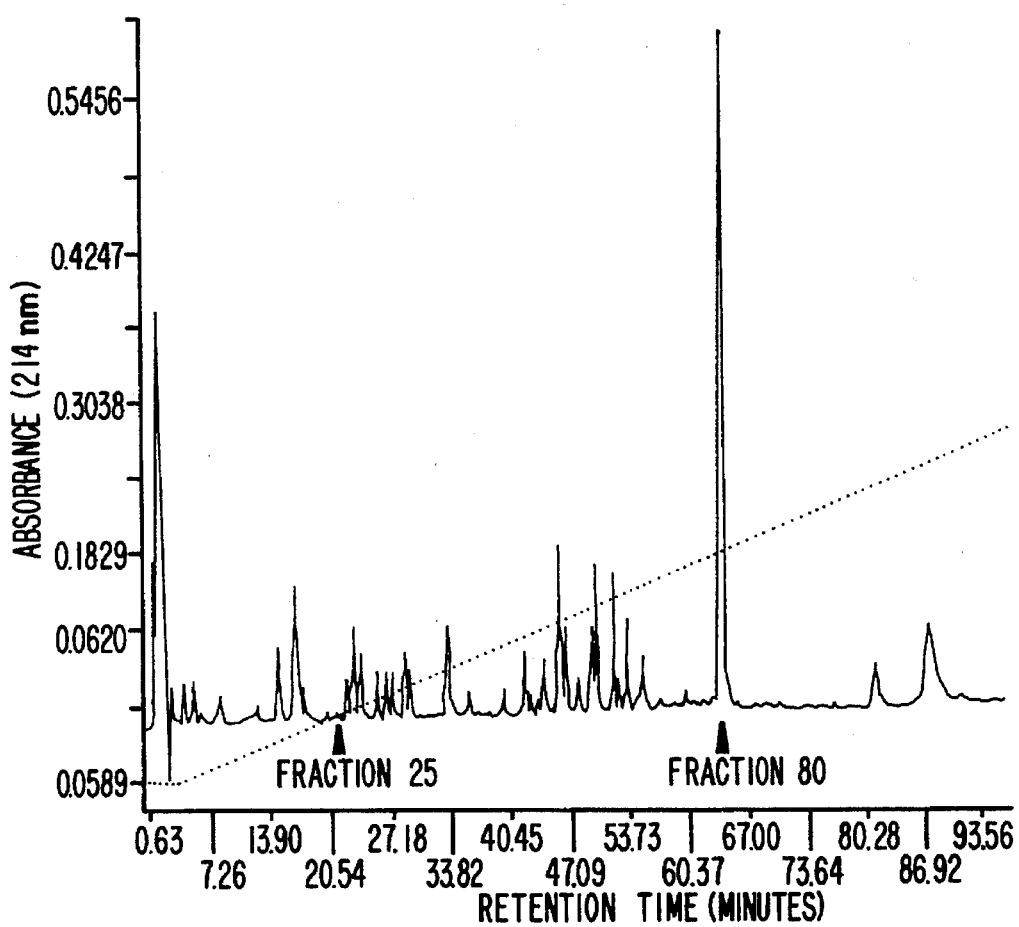
FIG. 3 HPLC and mass spectra of biotinylated peptides. Recombinant human tissue factor lacking the cytoplasmic domain, expressed and purified from *E. coli* was digested with TPCK-trypsin. The digest was fractionated by HPLC. The peaks absorbing at 214 nm (upper panel) were manually collected, concentrated by evaporation and redissolved in water. The HPLC peaks containing biotinylated peptides were detected by spotting 1 microliter of the peptide solution from each peak on nitrocellulose and using avidin conjugated with alkaline phosphatase as the detecting reagent according to standard Western blot protocols. Fractions 25 and 80 yielded intensely staining spots (not shown). Mass spectra of fractions 25 and 80 taken from a Biolon 20 'time of flight' mass spectrometer (middle and lower panels respectively) yielded peaks corresponding to putative biotinylated TF derived peptides (shown by arrows). The peaks of mass 907.5, 674.6 (fraction 25) and 2597.0 (fraction 80) each correspond to the calculated mass of a monobiotinylated TF tryptic peptide from the region of the TF sequence shown (bottom). The tryptic monobiotinylated fragments identified by mass spectrometry are underlined and the calculated ionic masses are indicated. Lysine residues 165 and 166 which were inferred to have been biotinylated are indicated. (The predicted peptide sequences in fraction 25 were confirmed by Edman sequencing). The minor peak in fraction 25 (929.7) has a mass compatible with its being the sodium adduct of the major peak (907.5). The mass of major peak in fraction 80 (5184.4) corresponds to the TF tryptic fragment spanning residues 75–122 (calculated mass 5183.6). The peak at 652.3 does not correspond to that of a TF tryptic fragment. Its identity is not known.
Figure 3B:
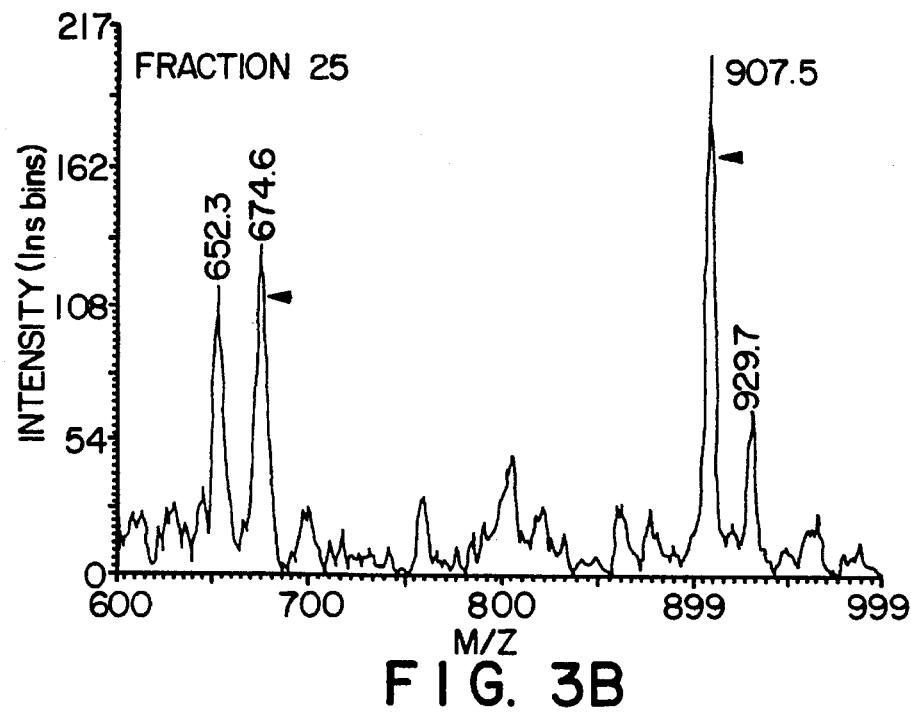
Figure 3C:
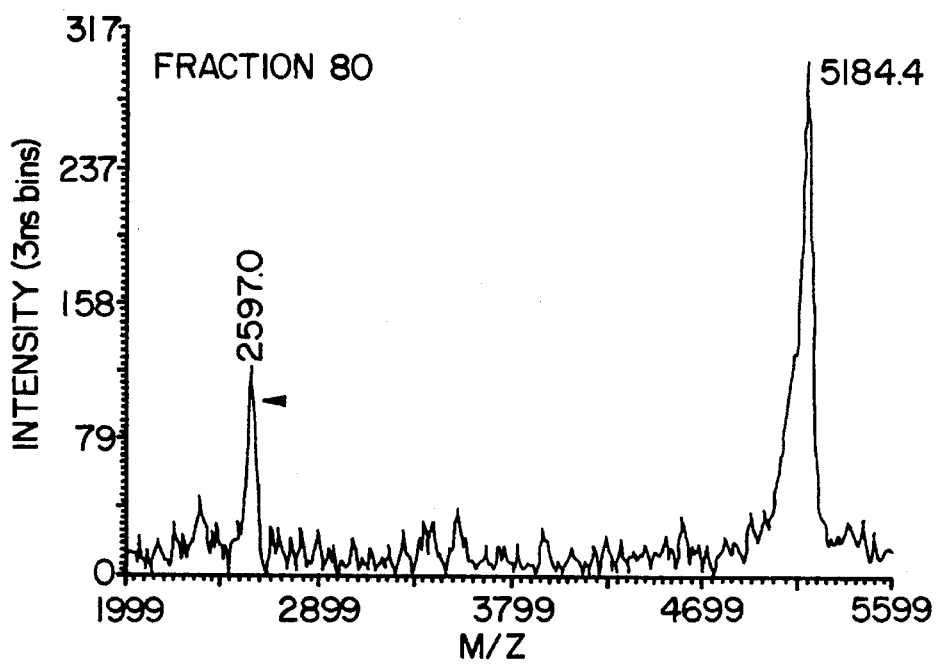
Figure 3D:
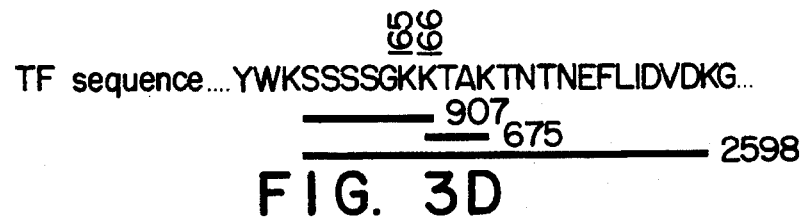

Upper panel: 293 cells transfected to express wild-type or mutant ('ala-ala') TF were washed twice with Buffer A (10 mM Hepes, 137 mM NaCl, 4 mM KCl, 11 mM glucose, pH 7.4) containing 10 mM EDTA and three times with Buffer A. Transfected and mock transfected cells were then incubated with 50 nM $^{125}$-I labelled factor VII in Buffer A containing 5 mM CaCl$_2$ and 0.5% BSA. After 1 h at 37° C., unbound factor VII/VIa was removed by three washes with Buffer A containing 5 mM CaCl$_2$. Bound factor VII/VIIa was then eluted from the cells by incubating for 5 min in Buffer A containing 10 mM EDTA. $^{125}$-I labelled factor VII alone (incubated in buffer without cells—lane 1), was subjected to SDS-polyacrylamide gel electrophoresis along with $^{125}$-I-factor VII eluting off cells transfected with wild type TF (lane 2), cells transfected with the K165A, K166A TF mutant (lane 3), and mock transfected cells (lane 4). The samples were reduced with DTT to show cleavage of bound factor VII. The positions of the molecular weight standards are indicated. The dried gel was autoradiographed.

Lower panel: The activity of wild-type TF in a chromogenic assay (O'Brien et al., supra) was used as a reporter of apparent factor VII concentration in the presence of increasing concentrations of mutant TF ('ala-ala'). Relipidation mixtures containing 0.001 picomoles/200 µl incubation of wild type TF and varying amounts of mutant K165A, K166A TF were assayed for activity using a limiting concentration of factor VII (0.1 picomole/200 µl incubation). The values for 'apparent [factor VII]' were dedved from a standard curve of activity of 0.001 picomole of TF in varying concentrations of factor VII.

DETAILED DESCRIPTION OF THE PREFERRED EMBODIMENTS

I. Definitions

In general, the following words or phrases have the indicated definition when used in the description, examples, and claims.

The term "tissue factor protein" is defined as a protein or glycoprotein capable of inducing blood coagulation through its interaction with plasma factor VII/VIIa on cell surface membranes (see eg. Fisher et al, *Thrombosis Research* 48:89–99 (1987)). Tissue factor protein is distinct from tissue factor (TF) or tissue thromboplastin of the prior art in that it lacks the naturally occurring lipid portion of the complex.

The term "tissue factor protein mutant" is defined as a polypeptide having at least qualitative biological activity in common with the polypeptide of FIG. 1 (SEQ. ID NO 1). The qualitating biological activity referred to is the capacity to neutralize the ability of tissue factor to induce blood coagulation. By "capable of neutralizing the ability of tissue factor to induce coagulation" is meant inhibiting any available tissue factor, from whatever source, from inducing blood coagulation through the extrinsic coagulation pathway (see e.g. Bach, R., *CRC Crit. Rev Biochem.* 23:339–368 (1988)). Without intending to be limited to any particular theory or mechanism, the following brief explanation is provided to aid in the understanding of how a tissue factor mutant can be capable of inhibiting coagulation. It is believed that by mutating certain amino acid residues of tissue factor protein, a "mutant confomer cofactor" is produced that is capable of binding to the enzyme factor VII/VIIa, but the "mutant confomer cofactor"-enzyme complex so formed is incapable of catalyzing the conversion of substrate (factor X) to product (factor Xa). Thus the tissue factor protein mutant of the instant invention is believed to compete with any wild-type tissue factor for the cofactor binding site on factor VII/VIIa, thereby neutralizing or preventing the tissue factor from acting as a cofactor in the coagulation cascade. As will be appreciated from the foregoing, the term inhibit or neutralize is a relative term. Thus the terms neutralize or inhibit when used to describe the biological activity of the instant tissue factor protein mutant means a mutant that when added in a 10-fold molar excess to wild-type tissue factor in a standard chromogenic assay (see e.g. Roy, S., *J. Biol. Chem.* 266:4665–4668 (1991) and O'Brien, D., et al., *J. Clin. Invest.*, 82:206–212 [1988]) produces at least a 50% inhibition of the conversion of factor X to Xa in the presence of factor VII and other necessary reagents. Preferably the tissue factor protein mutant will produce at least a 50% inhibition at a 5-fold molar excess and most preferably at a 2-fold molar excess. The very most preferred tissue factor protein mutant will produce at least 50% inhibition of the conversion of factor X to Xa when present in a 1:1 stoichiometdc ratio with wild type tissue factor protein.

The invention also contemplates a tissue factor protein mutant having at least the qualitative biological activity defined above and having at least 75% amino acid sequence homology with the polypeptide of FIG. 1 (SEQ ID NO. 1), or the polypeptide of FIG. 1 (SEQ ID NO. 7) lacking the cytoplasmic domain (amino acid residues from about 243 to 263), or soluble forms of the polypeptide of FIG. 1 (SEQ ID NO. 7) lacking both the cytoplasmic and functional transmembrane domain (amino acid residues from about 220 to 243).

The term "about", when used to modify amino acid residue numbers, means within 10 residues. Thus, for example, tissue factor protein mutants having the cytoplasmic domain deleted defined as from "about" amino acid residue 243 to 263 means a range of from 233–263 to 253–263.

Included within the scope of the tissue factor protein mutant as that term is used herein are tissue factor protein mutants having the translated or translated mature amino acid sequences of the rat, mouse or other mammalian tissue factor protein mutants, deglycosylated or unglycosylated derivatives of mammalian tissue factor protein mutants, homologous amino acid sequence variants of the sequence of FIG. 1 (SEQ ID NO 1), and homologous in vitro-generated variants and derivatives of the tissue factor protein mutants, that are capable of exhibiting a biological activity in common with the tissue factor protein mutant of FIG. 1 (SEQ ID NO 1). While the tissue factor protein mutant of FIG. 1 (SEQ ID NO. 1) is a membrane-bound polypeptide having a wild-type transmembrane and cytoplasmic domain, other forms, such as those containing a heterologous cytoplasmic and/or transmembrane domain(s) are also included within this definition.

Also included within the scope of the term tissue factor protein mutant is a polypeptide or protein encoded by the human tissue factor protein mutant nucleotide sequence set forth in FIG. 1 (SEQ ID NO. 1); fragments thereof having at least 15 and preferably at least 30 amino acid residues; amino acid sequence variants of the FIG. 1 (SEQ ID NO. 1) sequence wherein an amino acid residue has been added to the N- or C-terminal, or inserted within the FIG. 1 (SEQ ID NO. 1) sequence or its fragment as defined above; and/or amino acid sequence variants of the FIG. 1 (SEQ ID NO. 1) sequence or its fragment as defined above wherein an amino acid residue of the FIG. 1 (SEQ ID NO. 1) sequence or fragment thereof has been substituted by another residue, including predetermined mutations ( e.g., site-directed or PCR mutagenesis); other animal species of tissue factor protein such as rabbit, rat, porcine, non-human primate, equine, murine, and ovine tissue factor protein routants and alleles and other naturally occurring variants of the foregoing and human sequences; and derivatives of the tissue factor protein mutant or its fragments as defined above wherein the tissue factor protein mutant or its fragments have been covalently modified by substitution, chemical, enzymatic, or other appropriate means, with a moiety other than a naturally occurring amino acid. It is understood that any of the fragments, variants, or mutants defined above will be capable of neutralizing the ability of endogenous or wild type tissue factor to induce blood coagulation. Tissue factor protein mutant amino acid sequence variants preferably will share at least about 80%, more preferably greater than 85% sequence homology with the translated sequence shown in FIG. 1 (SEQ ID NO. 1).

Homology with respect to a tissue factor protein mutant is defined herein as the percentage of amino acid residues in a candidate sequence that are identical with either; the amino acid residues in FIG. 1 (SEQ ID NO. 1), the amino acid residues of FIG. 1 (SEQ ID NO. 1) where residues about 243–263 are deleted, or the amino acid residues of FIG. 1 (SEQ ID NO. 1) where residues about 220–263 are deleted, after aligning the sequences and introducing gaps, if necessary, to achieve the maximum identity. No N- nor C-terminal extensions or deletions in the candidate sequence shall be construed as reducing identity.

Tissue factor protein mutant "nucleic acid" is defined as RNA or DNA containing greater than ten (10) bases that encodes a tissue factor protein mutant, is complementary to nucleic acid sequence encoding the tissue factor protein mutant, hybridizes to such nucleic acid and remains stably bound to it under stringent conditions, or encodes a polypeptide sharing at least 75% sequence identity, preferably at least 80%, and more preferably at least 85%, with the translated amino acid sequence shown in FIG. 1 (SEQ ID NO. 1). Preferably the DNA which hybridizes to the nucleic acid of FIG. 1 (SEQ ID NO. 1) contains at least 20, more preferably 40, and even more preferably 60 bases. Most preferably, the hybridizing DNA or RNA contains 45 or even more preferably 90 bases. Such hybridizing or complementary nucleic acid, however, is defined further as being novel under 35 U.S.C. §102 and unobvious under 35 U.S.C. §103 over any prior art nucleic acid including that which encodes, hybridizes under stringent conditions, or is complementary to nucleic acid encoding a known tissue factor protein mutant capable of neutralizing the ability of tissue factor to induce coagulation.

"Stringent conditions" are any of those that (1) employ low ionic strength and high temperature for washing, for example, 0.015M NaCl/0.0015M sodium citrate/0.1% NaDodSO$_4$(SDS) at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employing 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice in order to equate the sites.

An "exogenous" element is defined herein to mean nucleic acid sequence that is foreign to the cell, or homologous to the cell but in a position within the host cell nucleic acid in which the element is ordinarily not found.

As used herein, the expressions "cells of" "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction Enzyme Digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al. (*Molecular Cloning: A Laboratory Manual* New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9:6103–6114 (1981), and Goeddel et al., *Nucleic Acids Res*, 8:4057 (1980).

"Southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrecellulose, nylon, or another suitable membrane supports for analysis with a radiolabeled, biotinylated or enzyme-labeled probe as described in sections 9.37–9.52 of Sambrook et al, supra.

"Northern analysis" is a method used to identify RNA sequences that hybridize to a known probe such as an oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrecellulose, nylon, or other suitable membrane, and hybridized with the probe, using standard techniques well known in the art such as those described in sections 7.39–7.52 of Sambrook et al., supra.

"Ligation" refers to the process of forming phosphodiester bonds between two nucleic acid fragments. To ligate the DNA fragments together, the ends of the DNA fragments must be compatible with each other. In some cases, the ends will be directly compatible after endonuclease digestion. However, it may be necessary to first convert the staggered ends commonly produced after endonuclease digestion to blunt ends to make them compatible for ligation. To blunt the ends, the DNA is treated in a suitable buffer for at least 15 minutes at 15C. with about 10 units of the Klenow fragment of DNA polymerase I or T4 DNA polymerase in the presence of the four deoxyribonucleotide triphosphates. The DNA is then pudfied by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The lineadzed fragment is then treated with bacterial alkaline phosphatase, or calf intestinal phosphatase to prevent self-ligation during the ligation step.

"Preparation" of DNA from cells means isolating the plasmid DNA from a culture of the host cells. Commonly used methods for DNA preparation are the large and small scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published 4 May 1988, or via deoxynucleoside H-phosphonate intermediates as described by Froehler et al., *Nucl. Acids Res*, 14:5399–5407 [1986]). They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., *PCR Technology*, (Stockton Press, New York, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

II. The Discovery Leading To The Invention

This invention is the result of the unexpected discovery that the amino-reactive cross-linking reagent (3,3'-dithiobis-sulfosuccinimidylpropionate) [DTSSP]) when used to cross-link tissue factor protein (TF) molecules on the cell surface (Roy, S. et al., *J. Biol. Chem.* 266:4665–4668 [1991]), was found to abolish TF activity in an assay which monitors the ability of factor VIIa to convert zymogen factor X to its active form Xa (O'Brien, D. P. et al., *J. Clin. Invest.* 82:206–211 [1988]). The protein biotinylation reagent sulfosuccinimidobiotin (sulfo-NHS-biotin), which has the same amino-reactive (capable of reacting with lysyl ε-amino and the free amino terminus of proteins) N-hydroxysuccinimide group as DTSSP, also inactivated TF (FIG. 2).

In order to determine whether this inactivation was due to the modification of one or more particularly susceptible lysine residue(s), purified TF, inactivated by treatment with 0.1 mM sulfo-NHS-biotin was digested with trypsin and subjected to HPLC analysis. It was possible to isolate those HPLC fractions which contained biotinylated peptide(s) by utilizing a dot-blot procedure using avidin conjugated with alkaline phosphatase as the detecting reagent. Mass spectrometry of two of the most intensely staining HPLC peaks (fractions 25 and 80; shown in FIG. 3—middle and lower panels respectively) predicted putative monobiotinylated (biotin contributes 226.3 to the molecular weight of the peptide) peptides corresponding to the overlapping peptide sequences 'Ser- Ser-Ser-Ser-Gly-Lys-Lys' (residues 160–166), 'Lys-Thr-Ala-Lys' (residues 166–169) and 'Ser-Ser-Ser-Ser-Gly-Lys-Lys-Thr-Ala-Lys-Thr-Asn-Thr-Asn-Glu-Phe-Leu-Ile-Asp-Val-Asp-Lys' (residues 160–181) (as shown in SEQ ID NO 1). Edman sequencing of fraction 25 confirmed the presence of the sequence 'Ser-Ser-Ser-Ser-Gly-X-Lys'. A lower yield of the sequence 'X-Thr-Ala-Lys' was also obtained. A peak was seen in cycle 6 on the phosphothiohydantoin chromatogram which eluted between histidine and tyrosine and was inferred to correspond to biotinylated lysine-165.

Figure 4A:
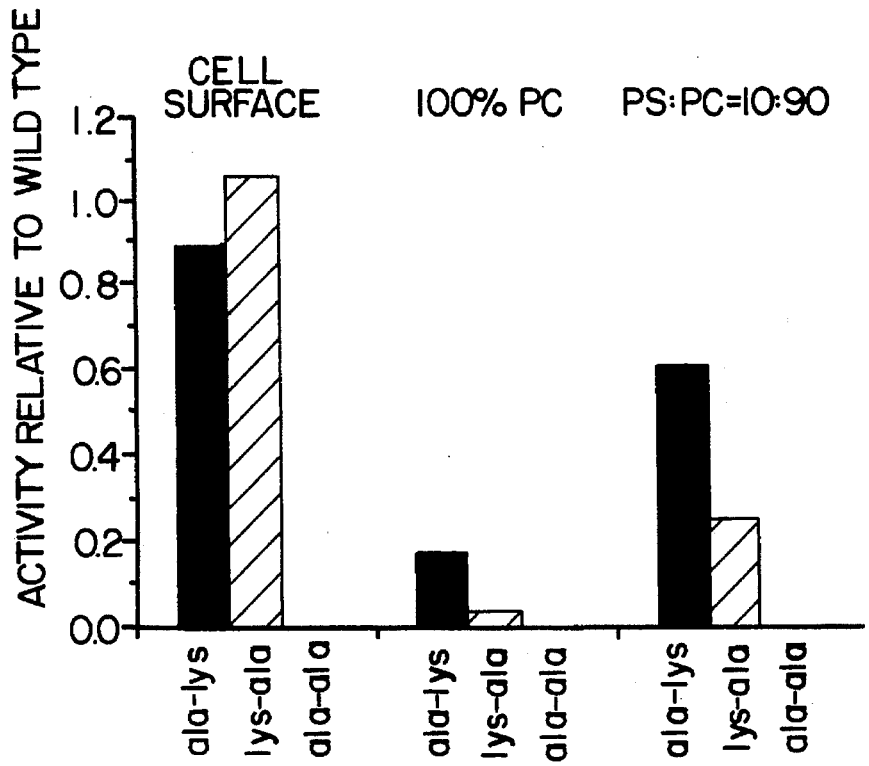
FIG. 4 Effect of phospholipid environment on the activities of wild-type and mutant TF. Wild type TF cDNA cloned in a mammalian expression vector (pCISTF1) or mutated TF cDNAs cloned in the plasmid pRK5 were used to transfect human kidney 293 cells using the calcium phosphate precipitation method. After 24 hours the cells were collected and the intact cells assayed for TF activity. To test for activity following relipidation, the cells were lysed using 1% Triton X-100 in 20 mM Tris. HCl, 130 mM NaCl, pH 7.4 (TBS), the TF antigen expression levels determined by Elisa, and the lysate diluted in TBS containing 0.2% BSA to 10 ng/ml before assaying in relipidation mixtures (O'Brien et al., supra) containing varying ratios of phosphatidylserine (PS): phosphatidylcholine (PC). The activity of the K165A, K166A mutant on the cell surface and in 100% phosphatidylcholine was not significantly above background (intact mock transfected cells or dilutions of lysates of mock transfected cells, respectively).
Figure 4B:
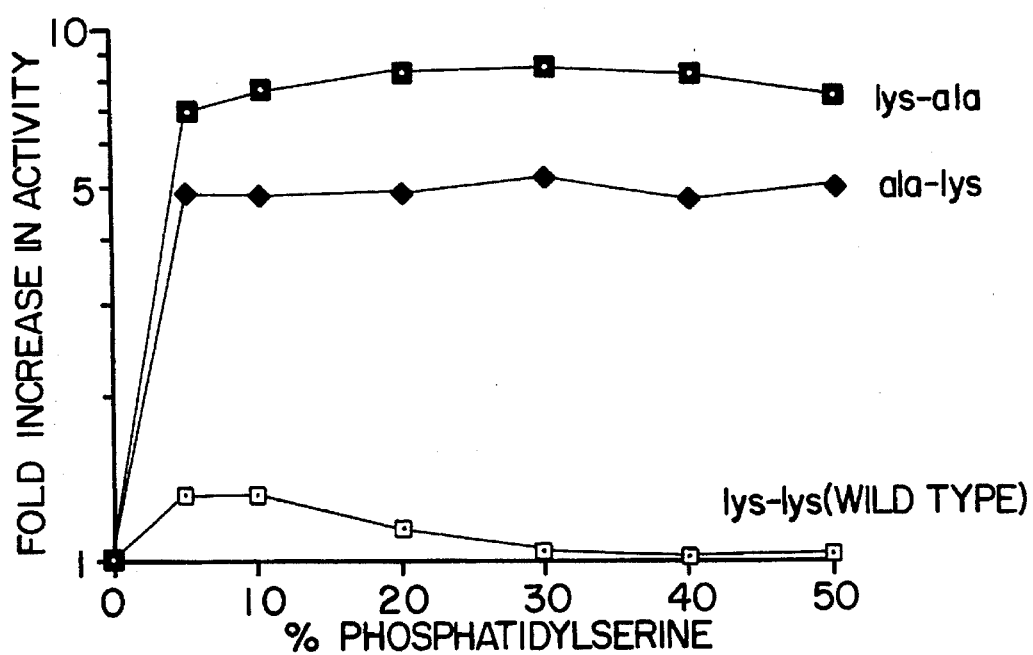

Since it was determined that lysine 165 (and possibly lysine 166) had been modified in human tissue factor inactivated by sulfo-NHS-biotin, site-directed mutagenesis was conducted to determine whether conversion of one or both lysines (165 and 166) to alanines would inactivate TF. Lysine 169 was not mutated because rabbit TF, which can function as a cofactor in human plasma, and mouse TF have non-conserved substitutions to threonine and isoleucine respectively at the corresponding position (Andrews, B., et al., *Gene*, 98:265–269 [1991]), whereas lysines 165 and 166 are conserved. The activities of these mutants were determined using intact transfected cells in a chromogenic assay, or by detergent solubilizing transfected cells and assaying for activity following 'relipidation' with phospholipid mixtures (O'Brien, D. P. et al., supra) (FIG. 4). The specific activities were determined by using a tissue factor ELISA to quantitate protein expression levels.

For the purposes of this application, the following notation is used to describe tissue factor protein mutants. The location of a particular amino acid in the polypeptide chain of tissue factor protein is identified by a number. This number designates to the amino acid position in the amino acid sequence of the mature, wild-type tissue factor polypeptide. The numerical designation used herein is that of the amino acid sequence of human tissue factor protein as described by Fischer et al., *Thrombosis Res.*, 48:89–99 (1987). It will be understood that similarly positioned residues in variant tissue factor protein molecules are designated by these numbers even though the actual residue number is not so numbered clue to deletions or insertions in the molecule. This will occur with fragments, alleles, and site-directed insertional or deletional variants. The amino acids are identified using the standard one letter code (see Stryer, *Biochemistry*, 3rd Ed., W. H. Freeman and Co., New York, [1988]). Substituted amino acids are designated by identifying the naturally occurring amino acid on the left side of the number which denotes the position of that amino acid, and identifying the substituted amino acid on the right side of the number. For example, replacing the amino acid lysine (K) at position 165 of tissue factor protein with alanine (A) would be designated as K165A. For multiple mutants, a comma "," is used to separate the sites of mutation within a polypeptide. Thus, for example, the double mutant of tissue factor protein in which lysines 165 and 166 are both converted to alanines is designated K165A, K166A.

The double K165A, K166A TF mutant ('ala-ala') had undetectable to very low activity in either of the above-described assays. The single K165A TF ('ala-lys') and K166A TF ('lys-ala') routants appeared as active as wild-type TF when expressed on the cell surface. However, in a relipidation assay where the only phospholipid used was phosphatidylcholine (PC), the single mutants had only 2–5% of the activity of the wild type molecule. Since it was known that relipidation mixtures containing up to 40% of the negatively charged phospholipid phosphatidylserine (PS) enhance TF activity (Bach, R. et al., *Biochemistry* 25: 4007–4020 [1986]), the effect of PS on the activity of the mutant tissue factors was determined. The activities were found to peak at between 5–40% PS content of the PS/PC mixtures. Although full activity could not be restored in these mutants merely by the addition of PS, the effect of adding PS was much more pronounced on the K165A TF and K166A TF mutants than on the wild type TF molecule.

Figure 5A:
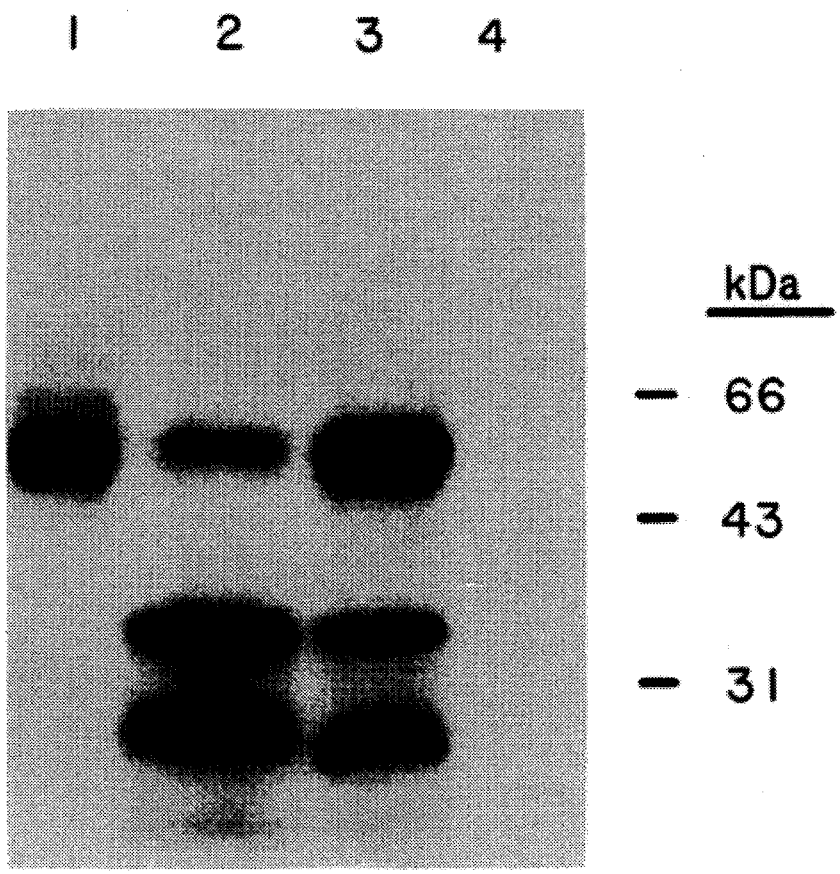
FIG. 5 Binding of factor VII to K165A, K166A TF mutant and inhibition of wild-type TF activity.
Figure 5B:
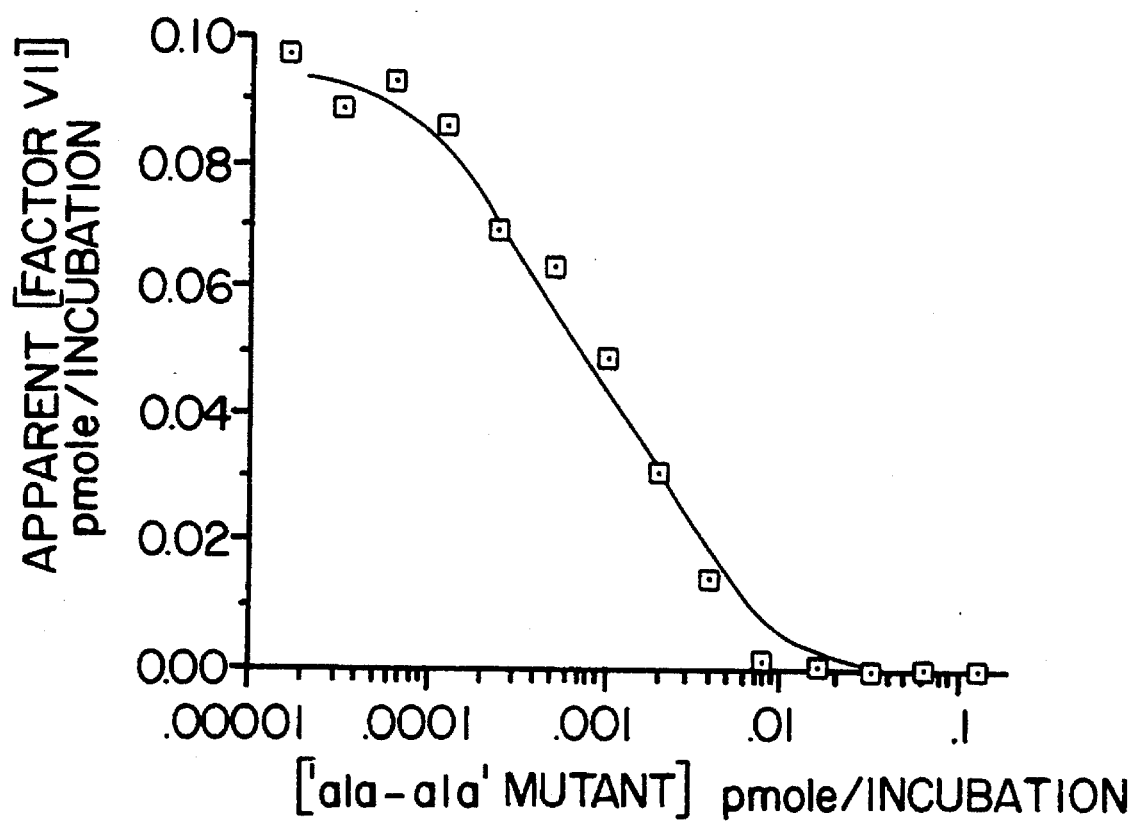

The inactive TF mutant K165A, K166A transiently expressed on the cell surface was found to bind factor VII (FIG. 5—upper panel) and to compete for factor VII with wild-type TF in a relipidation assay (FIG. 5—lower panel) where 50% inhibition of wild-type TF activity was seen when wild-type and mutant TF were present at a 1:1 stoichiometric ratio. Moreover, factor VII when bound to cells expressing the K165A, K166A TF double mutant, although functionally inactive, underwent a similar cleavage to a two-chain disulfide linked form as was seen with factor Vii bound to cells expressing wild-type TF. A similar cleavage has previously been shown to be due to intrinsic factor Xa activity (Fair, D. S., & MacDonald, M. J., *J. Biol, Chem.*, 262:11692–11698).

Without intending to be limited to any particular mechanism, the following explanation is provided to aid in understanding of the foregoing results. It has recently been proposed (Bach, R. & Rifkin, D. B., *Proc. Natl. Acad. Sci. USA* 87:6995–6999 [1990]) that the transfer of phosphatidylserine from the inner to the outer leaflet of the cell membrane by a calcium calmodulin dependent mechanism is necessary for the unmasking of TF activity at sites of tissue injury. The mechanism by which phosphatidylserine enhances TF activity is not known. Kinetic and binding data do not support the notion that a more negatively charged membrane recruits factor VIINIIa by interacting with its 'Gla' domain using $Ca^{2+}$ 'bridges' (Nemerson, Y., *Blood* 71:1–8). Thus, the large difference in activity of the K165A TF and K166A TF mutants when tested in a phosphatidylcholine relipidation system as compared to the cell surface, and the absence of activity of the K165A, K166A TF mutant, could indicate that lysines 165 and 166 constitute the protein component responsible for a charge mediated interaction with the cell membrane. This interaction may enable the enzyme-cofactor (factor VIIa-TF) complex to adopt a conformation capable of efficiently cleaving factor X, either by facilitated substrate binding, or increased catalytic efficiency. Whether the membrane component involved in this proposed interaction is phosphatidylserine or other negatively charged membrane components such as sulphated glycosaminoglycans like heparin (which also increases tissue factor activity (Aimus, F. E., et al., *Thromb. Haemostas.*, 62:1067–1073 [1989]) remains to be determined.

III. Suitable Methods for Practicing the Invention

The Tissue Factor Protein Mutant

The tissue factor protein mutant of the instant invention is capable of neutralizing the ability of tissue factor protein to induce blood coagulation. As set forth in greater detail below, tissue factor protein mutant of FIG. 1 (SEQ ID NO: 1) and variants thereof can be produced by procedures known in the art that have the same qualitative biological activity as the polypeptide of FIG. 1 (SEQ ID NO: 1). Variants having the same qualitative biological activity but a higher affinity for the TF-factor VII binding site are included within the scope of the instant intervention. These latter variants can be produced and screened for by procedures known in the art; Cunningham, B., et al., *Science*, 247:1461–1465 (1990), and Bass, S., et al., *Proteins: Structure, Function and Genetics*, 8:309–314 (1990).

Amino Acid Sequence Variants of the Tissue Factor Protein Mutant

Amino acid sequence variants of the tissue factor protein mutant are prepared by introducing appropriate nucleotide changes into the tissue factor protein mutant DNA, or tissue factor protein DNA ( see Fisher et al. supra). Such variants include, for example, deletions from, or insertions or substitutions of, residues within the amino acid sequence shown for the human tissue factor protein mutant in FIG. 1 (SEQ ID NO: 1). Any combination of deletion, insertion, and substitution can be made to ardve at the final construct, provided that the final construct possesses the desired characteristics. Excluded from the scope of this invention are tissue factor protein mutant variants or polypeptide sequences that are not novel and unobvious over the prior art. The amino acid changes also may alter post-translational processes of the tissue factor protein mutant, such as changing the number or position of glycosylation sites, altering the membrane anchoring characteristics, and/or altering the intra-cellular location of the tissue factor protein mutant by inserting, deleting, or otherwise affecting the leader sequence of the native tissue factor protein mutant.

In designing amino acid sequence variants of tissue factor protein mutant, the location of the mutation site and the nature of the mutation will depend on the tissue factor protein mutant characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the tissue factor protein mutant polypeptide that are preferred locations for mutagenesis is called "alanine scanning mutagenesis" as described by Cunningham and Wells (*science*, 244:1081–1085 [1989]). Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed tissue factor protein mutant variants are screened for the optimal combination of desired activity.

There are two principal variables in the construction of amino acid sequence variants: the location of the mutation site and the nature of the mutation. These are vadants based on the FIG. 1 (SEQ. ID NO: 1) sequence. In general, the location and nature of the mutation chosen will depend upon the tissue factor protein mutant characteristic to be modified.

Amino acid sequence deletions generally range from about 1 to 30 residues, more preferably about 1 to 10 residues, and typically are contiguous. The number of consecutive deletions will be selected so as to preserve the tertiary structure of the tissue factor protein mutant in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the tissue factor protein mutant sequence) may range generally from about 1 to 10 residues, more preferably 1 to 5, most preferably 1 to 3. Examples of terminal insertions include the tissue factor protein mutant with a heterologous N-terminal signal sequence to the N-terminus of the tissue factor protein mutant molecule to facilitate the secretion of the mature tissue factor protein mutant from recombinant host cells. Such signal sequences generally will be obtained from, and thus homologous to, the intended host cell species. Suitable sequences include STII or lpp for *E. coli*, alpha factor for yeast, and viral signals such as herpes gD for mammalian cells.

Other insertional variants of the tissue factor protein mutant include the fusion to the N- or C-terminus of the tissue factor protein mutant of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

Another group of variants are amino acid substitution variants. These variants have at least one amino acid residue in the tissue factor protein mutant molecule removed and a different residue inserted in its place. The sites of greatest interest for substitutional mutagenesis include sites identified as the active site(s) of the tissue factor protein mutant, and sites where the amino acids found in the tissue factor protein mutant from various species are substantially different in terms of side-chain bulk, charge, and/or hydrophobicity.

Other sites of interest are those in which particular residues of tissue factor protein and the instant mutants obtained from various species are identical. These positions may be important for the biological activity of the tissue factor protein mutant. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; norleucine | Leu |
| Leu (L) | norleucine; Ile; Val Met; Ala; Phe | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Trp (W) | Tyr | Tyr |

TABLE 1-continued

| Original Residue | Exemplary Substitutions | Preferred Substitutions |
| --- | --- | --- |
| Tyr (Y) | Trp; Phe; Thr; Ser | Phe |
| Val (V) | Ile; Leu; Met; Phe Ala; norleucine | Leu |

Substantial modifications in function or immunological identity of the tissue factor protein mutant are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Non-conservative substitutions will entail exchanging a member of one of these classes for another. Such substituted residues may be introduced into regions of the tissue factor protein mutant that are homologous with other tissue factor proteins, or, more preferably, into the non-homologous regions of the molecule.

Any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of tissue factor protein mutant also may be substituted, generally with serine, to improve the oxidative stability of the molecule and prevent aberrant crosslinking. DNA encoding amino acid sequence variants of the tissue factor protein mutant is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared vadant or a non-variant version of the tissue factor protein mutant. These techniques may utilized tissue factor protein mutant nucleic acid (DNA or RNA), or nucleic acid complementary to the tissue factor protein mutant nucleic acid.

Oligonucleotide-mediated mutagenesis is a preferred method for preparing substitution, deletion, and insertion variants of tissue factor protein mutant DNA. This technique is well known in the art as described by Adelman et al., *DNA*, 2:183 (1983). Alternatively, the Altered Sites™ kit from Promega Corporation may be used, to generate mutants. Briefly, the tissue factor protein mutant DNA is altered by hybridizing an oligonucleotide encoding the desired mutation to a DNA template, where the template is the single-stranded form of a plasmid or bacteriophage containing the unaltered or native DNA sequence of the tissue factor protein mutant. After hybridization, a DNA polymerase is used to synthesize an entire second complementary strand of the template that will thus incorporate the oligonucleotide primer, and will code for the selected alteration in the tissue factor protein mutant DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75:5765 [1978]).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the tissue factor protein mutant, and the other strand (the original template) encodes the native, unaltered sequence of the tissue factor protein mutant. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxydbocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding tissue factor protein mutants with more than one amino acid to be substituted may be generated in one of several ways if the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of tissue factor protein mutant. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µl. The reaction mixture is overlaid with 35 µl mineral oil. The reaction is denatured for 5 minutes at 100° C., placed briefly on ice, and then 1 µl *Therrmus aquaticus* (Taq) DNA polymerase (5 units/µl, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:
  30 sec. 94° C.,
  30 sec. 55° C., and
  30 sec. 72° C.

At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (*Gene*, 34:315 [1985]). The starting material is the plasmid (or other vector) comprising the tissue factor protein mutant DNA to be mutated. The codon(s) in the tissue factor protein mutant DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the tissue factor protein mutant DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated tissue factor protein mutant DNA sequence.

Insertion of DNA into a Cloning Vehicle

The cDNA encoding a variant tissue factor protein mutant is inserted into a replicable vector for further cloning (amplification of the DNA) or for expression, that is, production of protein from the DNA. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the tissue factor protein mutant DNA that is inserted into the vector. The native pro tissue factor protein mutant DNA encodes a signal sequence at the amino terminus (5' end of the DNA) of the polypeptide that is cleaved during post-translational processing of the polypeptide to form the mature tissue factor protein mutant polypeptide. Tissue factor protein mutant is not however secreted from the cell as it contains a membrane anchoring domain near the carboxyl terminus of the polypeptide. Thus, to form a secreted or soluble version of tissue factor protein mutant, the carboxyl terminal (cytoplasmic) domain of the molecule, including the membrane anchoring domain, is ordinarily deleted. This truncated variant tissue factor protein mutant polypeptide may be secreted from the cell, provided that the DNA encoding the truncated vadant retains the amino terminal signal sequence.

The tissue factor protein mutant of this invention may be expressed not only directly, but also as a fusion with a heterologous polypeptide. The heterologous protein may be a signal sequence or other polypeptide having a specific cleavage site at the N-terminus of the mature protein or polypeptide. In general, the signal sequence may be a component of the vector, or it may be a part of the tissue factor protein mutant DNA that is inserted into the vector. Included within the scope of this invention are tissue factor protein mutants with the native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native tissue factor protein signal sequence, the signal sequence is substituted by a prokaryotic signal sequence selected, for example, from the group of the alkaline phosphatase, penicillinase, Ipp, or heat-stable enterotoxin II leaders. For yeast secretion the native tissue factor protein signal sequence may be substituted by the yeast invertase, alpha factor, or acid phosphatase leaders. In mammalian cell expression the native signal sequence is satisfactory, although other mammalian signal sequences may be suitable. Optionally the heterologous (to tissue factor protein mutant) protein may be a coat protein of a virus, phage, or helper phage such as M13K07.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 u plasmid odgin is suitable for yeast, and various viral odgins (SV40, polyoma, adenovirus, VSV or BPV) are useful for odgins of replication in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the tissue factor protein mutant DNA. However, the recovery of genomic DNA encoding the tissue factor protein mutant is more complex than that of an exogenously replicated vector because restriction enzyme digestion is required to excise the tissue factor protein mutant DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al, *J. Molec. Appl. Genet.,* 1:327 [1982]), mycophenolic acid (Mulligan et al., *Science,* 209:1422 [1980]) or hygromycin (Sugden et al., *Mol. Cell. Biol.,* 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the tissue factor protein mutant nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the tissue factor protein mutant. Amplification is the process by which genes in greater demand for the production of a protein critical for growth are reiterated in tandem within the chromosomes of successive generations of recombinant cells. Increased quantities of the tissue factor protein mutant are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77:4216 [1980]. The transformed cells are then exposed to increased levels of methotrexate. This leads to the synthesis of multiple copies of the DHFR gene, and, concomitantly, multiple copies of other DNA comprising the expression vectors, such as the DNA encoding the tissue factor protein mutant. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the tissue factor protein mutant, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282:39 [1979]; Kingsman et al., *Gene,* 7:141 [1979]; or Tschemper et al., *Gene,* 10:157 [1980]). The trp1 gene provides a selection marker for a mutant strain of yeast lacking the ability to grow in tryptophan, for example, ATCC No. 44076 or PEP4-1 (Jones, *Genetics,* 85:12 [1977] ). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the tissue factor protein mutant nucleic acid. Promoters are untranslated sequences located upstream (5') to the start codon of a structural gene (generally within about 100 to 1000 bp) that control the transcription and translation of a particular nucleic acid sequence, such as the tissue factor protein mutant, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the tissue factor protein mutant by removing the promoter from the source DNA by restriction enzyme digestion and inserting the isolated promoter sequence into the vector. Both the native tissue factor protein mutant promoter sequence and many heterologous promoters may be used to direct amplification and/or expression of the tissue factor protein mutant DNA. However, heterologous promoters are preferred, as they generally permit greater transcription and higher yields of expressed tissue factor protein mutant as compared to the native tissue factor protein mutant promoter.

Promoters suitable for use with prokaryotic hosts include the betalactamase and lactose promoter systems (Chang et al., *Nature,* 275:615 [1978]; and Goeddel et al., *Nature,* 281:544 [1979]), alkaline phosphatase, a tryptophan (trp) promoter system (Goeddel, *Nucleic Acids Res.,* 8:4057 [1980] and EP 36,776) and hybird promoters such as the tac promoter (deBoer et al., *Proc. Natl. Acad. Sci. USA,*

80:21–25 [1983]). However, other known bacterial promoters are suitable. Their nucleotide sequences have been published, thereby enabling a skilled worker operably to ligate them to DNA encoding the tissue factor protein mutant (Siebenlist et all, *Cell,* 20:269 [1980]) using linkers or adaptors to supply any required restriction sites. Promoters for use in bacterial systems also generally will contain a Shine-Dalgarno (S.D.) sequence operably linked to the DNA encoding the tissue factor protein mutant.

Suitable promoting sequences for use with yeast hosts include the promoters for 3-phosphoglycerate kinase (Hitzeman et al., *J. Biol. Chem.,* 255:2073 [1980]) or other glycolytic enzymes (Hess et al., *J. Adv. Enzyme Reg.,* 7:149 [1968]; and Holland, *Biochemistry,* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for realrose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Tissue factor protein mutant transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the tissue factor protein mutant sequence, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 (1978); Mulligan and Berg, *Science,* 209:1422–1427 (1980); Pavlakis et al., *Proc. Natl. Acad. Sci. USA,* 78:7398–7402 (1981). The immediate early promoter of the human cytomegalovirus is conveniently obtained as a HindIII E restriction fragment. Greenaway et al., *Gene,* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295:503–508 (1982) on expressing cDNA encoding immune interferon in monkey cells;, Reyes et al., *Nature,* 297:598–601 (1982) on expression of human_4-interfreon cDNA in mouse cells under the control of a thymidine kinase promoter from herpes simplex virus, Canaani and Berg, *Proc. Natl. Acad. Sci. USA,* 79:5166–5170 (1982) on expression of the human interferon_1 gene in cultured mouse and rabbit cells, and Gorman et al., *Proc. Natl. Acad. Sci. USA,* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the tissue factor protein mutant of this invention by higher eukaryotes is often increased by inserting an enhancer sequence into the vector. Enhancers are ds-acting elements of DNA, usually about from 10–300 bp, that act on a promoter to increase its transcription. Enhancers are relatively orientation and position independent having been found 5' (Laimins et al., *Proc. Natl. Acad. Sci. USA,* 78:993 [1981]) and 3' (Lusky et al., *Mol. Cell Bio.,* 3:1108 [1983]) to the transcription unit, within an intron (Banerji et al., *Cell.* 33:729 [1983]) as well as within the coding sequence itself (Osborne et al., *Mol. Cell Bio.,* 4:1293 [1984]). Many enhancer sequences are now known from mammalian genes (globin, elastase, albumin, alpha-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature,* 297:17–18 (1982) on enhancing elements for activation of eukaryotic promoters. The enhancer may be spliced into the vector at a position 5' or 3' to the tissue factor protein mutant DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the tissue factor protein mutant. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and relegated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 (1981) or by the method of Maxam et al., *Methods in Enzymology,* 65:499 (1980).

Particularly useful in the practice of this invention are expression vectors that provide for the transient expression in mammalian cells of DNA encoding the tissue factor protein mutant. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the tissue factor protein mutant that have tissue factor protein mutant-like activity.

Other methods, vectors, and host cells suitable for adaptation to the synthesis of the tissue factor protein mutant in recombinant vertebrate cell culture are described in Gething et al., *Nature*, 293:620–625 [1981]; Mantei et al., *Nature*, 281:40–46 [1979]; Levinson et al.; EP 117,060; and EP 117,058. A particularly useful plasmid for mammalian cell culture expression of the tissue factor protein mutant is pRK5 (EP pub. no. 307,247) or pSVI6B (U.S. Ser. No. 07/441,574 filed 22 Nov. 1989).

B. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aeruginosa*, Salmonella typhimurium, or *Serratia marcescans*. One preferred *E. coli* cloning host is *E. coli* 294 (ATCC 31,446), although other strains such as *E. coli* B, *E. coli* x1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for tissue factor protein mutant-encoding vectors. *Saccharomyces cerevisiae*, or common bakers yeast, is the most commonly used among lower eukaryotic host microorganisms. However, a number of other genera, species, and strains are commonly available and useful herein, such as *Schizosaccharomyces pombe* [Beach and Nurse, *Nature*, 290:140 (1981); EP 139,383 published May 2, 1985], Kluyveromyces hosts (U.S. Pat. No. 4,943,529) such as, e.g., *K. lactis* [Louvencourt et al., *J. Bacteriol.*, 737(1983)], *K. fragilis*, *K. bulgaricus*, *K. thermotolerans*, and *K. marxianus*, yarrowia [EP 402,226], *Pichia pastoris* [EP 183,070; Sreekrishna et al., *J. Basic Microbiol.*, 28:265–278 (1988)], Candida, *Trichoderma reesia* [EP 244,234], *Neurospora crassa* [Case et al., 76:5259–5263 (1979)] and filamentous fungi such as, e.g, Neurospora, Penicillium, Tolypocladium [WO 91/00357 published 10 Jan. 1991], and Aspergillus hosts such as A. nidulans [Ballance et al., *Biochem. Biophys. Res. Commun.*, 112:284–289 (1983); Tiiburn et al., *Gene*, 26:205–221 (1983); Yelton et al., *Proc. Natl. Acad. Sci. USA*, 81:1470–1474 (1984)] and *A. niger* [Kelly and Hynes, *EMBO J.*, 4:475–479 (1985)].

Suitable host cells for the expression of glycosylated tissue factor protein mutant polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6:47–55 (1988); Miller et al., in *Genetic Engineering*, Setlow, J. K. et al., eds., Vol. 8 (Plenum Publishing, 1986), pp. 277–279; and Maeda et al., *Nature*, 315:592–594 (1985). A variety of such viral strains are publicly available, e.g., the L-1 variant of *Autographa cafifornica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the tissue factor protein mutant DNA. Dudng incubation of the plant cell culture with *A. tumefaciens*, the DNA encoding tissue factor protein mutant is transferred to the plant cell host such that it is transfected, and will, under appropriate conditions, express the tissue factor protein mutant DNA. In addition, regulatory and signal sequences compatible with plant cells are available, such as the nopaline synthase promoter and polyadenylation signal sequences. Depicker et al., *J. Mol. Appl. Gen.*, 1:561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 [1977]); baby hamster kidney cells (BHK, ATCC CCL 10); Chinese hamster ovary cells/-DHFR (CHO, Urlaub and Chasin, *Proc. Natl. Acad. Sci. USA*, 77:4216 [1980]); mouse sertoli cells (TM4, Mather, *Biol. Reprod.*, 23:243–251 [1980]); monkey kidney cells (CV1 ATCC CCL 70); African green monkey kidney cells (VERO-76, ATCC CRL-1587); human cervical carcinema cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., 383:44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method described in sections 16.30–16.37 of Sambrook et al, supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130:946 (1977) and Hsiao et al., *Proc. Natl. Acad. Sci.(USA)*, 76:3829 (1979). However, other methods for introducing DNA into cells such as by nuclear injection, electroporation, or protoplast fusion may also be used.

C. Culturing the Host Cells

Prokaryotic cells used to produce the tissue factor protein mutant polypeptide of this invention are cultured in suitable media as described generally in Sambrook et al., supra.

The mammalian host cells used to produce the tissue factor protein mutant of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58:44 (1979), Barnes and Sato, *Anal. Biochem.*, 102:255 (1980), U.S. Pat. No. 4,767, 704; 4,657,866; 4,927,762; or 4,560,655; WO 90/03430; WO 87/00195; U.S. Pat. No. Re. 30,985; or copending U.S. Ser. No. 07/592,107 or 07/592,141, both filed in 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

D. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77:5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybdd duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

Antibodies useful for immunohistochemical staining and/or assay of sample fluids may be either monoclonal or polyclonal, and may be prepared in any mammal. Conveniently, the antibodies may be prepared against a native tissue factor protein mutant polypeptide or against a synthetic peptide based on the DNA sequences provided herein as described further in Section 4 below.

E. Purification of The Tissue Factor Protein Mutant Polypeptide

The soluble tissue factor protein mutant may be recovered from the culture medium as a secreted polypeptide. Alternatively, the mutant containing a transmembrane domain may be recovered from host cell iysates when directly expressed without a secreton/signal.

When the tissue factor protein mutant is expressed in a recombinant cell other than one of human origin, the tissue factor protein mutant is completely free of proteins or polypeptides of human origin. However, it is necessary to purify the tissue factor protein mutant from recombinant cell proteins or polypeptides to obtain preparations that are substantially homogeneous as to the tissue factor protein mutant. As a first step, the culture medium or lysate is centrifuged to remove particulate cell debris. The membrane and soluble protein fractions are then separated. The tissue factor protein mutant may then be purified from the soluble protein fraction and from the membrane fraction of the culture lysate, depending on whether the tissue factor protein mutant is membrane bound. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Tissue factor protein mutant variants in which residues have been deleted, inserted or substituted are recovered in the same fashion as the native tissue factor protein mutant, taking account of any substantial changes in properties occasioned by the variation. For example, preparation of a tissue factor protein mutant fusion with another protein or polypeptide, e.g. a bacterial or viral antigen, facilitates purification; an immunoaffinity column containing antibody to the antigen can be used to adsorb the fusion. Immunoaffinity columns such as a rabbit polyclonal anti-tissue factor protein mutant column can be employed to absorb the tissue factor protein mutant variant by binding it to at least one remaining immune epitope. A protease inhibitor such as phenyl methyl sulfonyl fluoride (PMSF) also may be useful to inhibit proteolytic degradation dudng purification, and antibiotics may be included to prevent the growth of adventitious contaminants. A preferred method of purification of tissue factor protein mutants is by immunoaffinity using a tissue factor protein or tissue factor protein mutant specific monoclonal antibody following the procedures set forth in Paborsky, L., et al., *Biochemistry,* 28:8072–8077 (1989), Morissey, J., et al., *Thromb. Res.,* 52:247–261 (1988), or Ruf, W., et al., *Blood,* 74:94a (1988). One skilled in the art will appreciate that purification methods suitable for tissue factor protein mutant may require modification to account for changes in the character of the tissue factor protein mutant or its variants upon expression in recombinant cell culture.

F. Covalent Modifications of Tissue Factor Protein Mutant Polypeptides

Covalent modifications of tissue factor protein mutant polypeptides are included within the scope of this invention. Both native tissue factor protein mutant and amino acid sequence vadants of the tissue factor protein mutant may be covalently modified. One type of covalent modification included within the scope of this invention is a tissue factor protein mutant polypeptide fragment. Tissue factor protein mutant fragments having up to about 40 amino acid residues may be conveniently prepared by chemical synthesis, or by enzymatic or chemical cleavage of the full-length tissue factor protein mutant polypeptide or tissue factor protein mutant variant polypeptide. Other types of covalent modifications of the tissue factor protein mutant or fragments thereof are introduced into the molecule by reacting targeted amino acid residues of the tissue factor protein mutant or fragments thereof with an organic derivatizing agent that is capable of reacting with selected side chains or the N- or C-terminal residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-B-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhyclrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking tissue factor protein mutant to a water-insoluble support matrix or surface for use in the method for purifying anti-tissue factor protein mutant antibodies, and vice versa. Commonly used crosslinking agents include, e.g., 1,1-bis-(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithiopropiomidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group.

Another type of covalent modification of the tissue factor protein mutant included within the scope of this invention comprises altering the native glycosylation pattern of the polypeptide. By altering is meant deleting one or more carbohydrate moieties found in the tissue factor protein mutant, and/or adding one or more glycosylation sites that are not present in the native tissue factor protein mutant.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the tissue factor protein mutant polypeptide is conveniently accomplished by altering the amino acid sequence such that it contains one or more of the above-described tri-peptide sequences (for N-linked glycosylation sites). The alteration may also be made by the addition of, or substitution by, one or more serine or threonine residues to the native tissue factor protein mutant sequence (for O-linked glycosylation sites). For ease, the tissue factor protein mutant amino acid sequence is preferably altered through changes at the DNA level, particularly by mutating the DNA encoding the tissue factor protein mutant polypeptide at preselected bases such that codons are generated that will translate into the desired amino acids. The DNA mutation(s) may be made using methods described above under the heading of "Amino Acid Sequence Variants of Tissue factor protein mutant Polypeptide".

Another means of increasing the number of carbohydrate moieties on the tissue factor protein mutant is by chemical or enzymatic coupling of glycosides to the polypeptide. These procedures are advantageous in that they do not require production of the polypeptide in a host cell that has glycosylation capabilities for N- and O- linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston (CRC *Crit. Rev. Biochem.*, pp. 259–306 [1981]).

Removal of carbohydrate moieties present on the tissue factor protein mutant polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact.

Chemical deglycosylation is described by Hakimuddin et al. (*Arch. Biochem. Biophys.*, 259:52 [1987]) and by Edge et al. (*Anal. Biochem.*, 118:131 [1981]). Enzymatic cleavage of carbohydrate moieties on polypeptides can be achieved by the use of a variety of endo- and exo-glycosidases as described by Thotakura et al. (*Meth. Enzymol.*, 138:350 [1987]).

Glycosylation at potential glycosylation sites may be prevented by the use of the compound tunicamycin as described by Duskin et al. (*J. Biol. Chem.*, 257:3105 [1982]). Tunicamycin blocks the formation of protein-N-glycoside linkages.

Another type of covalent modification of the tissue factor protein mutant comprises linking the tissue factor protein mutant polypeptide to various nonproteinaceous polymers, e.g. polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The tissue factor protein mutant also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposome, albumin microspheres, microemulsions, nano-particles and nanocapsules), or in macroemulsions. Such techniques are disclosed in *Remington's Pharmaceutical Sciences*, 16th edition, Osol, A., Ed., (1980).

Tissue factor protein mutant preparations are also useful in generating antibodies, as standards in assays for the tissue factor protein mutant (e.g. by labeling the tissue factor protein mutant for use as a standard in a radioimmunoassay, enzyme-linked immuneassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant tissue factor protein mutant, it will be appreciated that some screening of the recovered variant will be needed to select the optimal variant. For example, a change in the immunological character of the tissue factor protein mutant molecule, such as affinity for a given antibody, is measured by a competitive-type immunoassay. The variant is assayed for changes in the suppression or enhancement of its activity by comparison to the activity observed for native tissue factor protein mutant in the same assay. Other potential modifications of protein or polypeptide properties such as redox or thermal stability, hydrophobicity, susceptibility to proteolytic degradation, stability in recombinant cell culture or in plasma, or the tendency to aggregate with carriers or into multimers are assayed by methods well known in the art.

IV. Therapeutic Compositions and Administration of Tissue Factor Protein Mutant

Therapeutic formulations of tissue factor protein mutant are prepared for storage by mixing tissue factor protein mutant having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, octylglucoside, Pluronics or polyethylene glycol (PEG). Tissue factor protein mutant may also be admixed with phospholipids, including PS and PC, or used in conjunction with liposomes.

The tissue factor protein mutant to be used for in vivo administration must be sterile. This is readily accomplished by filtration through sterile filtration membranes, pdor to or following lyophilization and reconstitution. The tissue factor protein mutant ordinarily will be stored in lyophilized form or in solution.

Therapeutic tissue factor protein mutant compositions generally are placed into a container having a sterile access port, for example, an intravenous solution bag or vial having a stopper pierceable by a hypodermic injection needle.

The tissue factor protein mutant optionally is combined with or administered in concert with other agents such as: thrombolytics; streptokinase, urokinase, or t-PA, anticoagulants; hurudin, hirudin analogues, heparin, or Argatroban, and GP $II_bIII_a$ inhibitors for treatment of particular disorders such as myocardial infarction and coagulopathic disorders.

The route of tissue factor protein mutant administration is in accord with known methods, e.g. injection or infusion by intravenous, intraperitoneal, intracerebral, intramuscular, intraocular, intraarterial, or intralesional routes, or by sustained release systems as noted below. The tissue factor protein mutant is administered continuously by infusion or by bolus injection.

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogels [e.g., poly(2-hydroxyethyl-methacrylate) as described by Langer et al., *J. Biomed. Mater. Res.*, 15:167–277 [1981] and Langer, Chem. Tech., 12:98–105 [1982] or poly(vinylalcohol)], polylactides (U.S. Pat. No. 3,773,919, EP 58,481), copolymers of L-glutamic acid and gamma ethyl-L-glutamate (Sidman et al., *Biopolymers,* 22: 547–556 [1983]), non-degradable ethylene-vinyl acetate (Langer et al., supra), degradable lactic acid-glycolic acid copolymers such as the Lupron Depot™ (injectable micropheres composed of lactic acid-glycolic acid copolymer and leuprolide acetate), and poly-D-(−)-3-hydroxybutyric acid (EP 133,988). While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thiodisulfide interchange, stabilization may be achieved by modifying sulfhydryl residues, lyophilizing from acidic solutions, controlling moisture content, using appropriate additives, and developing specific polymer matrix compositions.

Sustained-release tissue factor protein mutant compositions also include liposomally entrapped tissue factor protein mutant. Liposomes containing tissue factor protein mutant are prepared by methods known per se: DE 3,218,121; Epstein et al., *Proc. Natl. Acad. Sci. USA,* 82:3688–3692 (1985); Hwang et al., *Proc. Natl. Acad. Sci. USA,* 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal tissue factor protein mutant therapy.

An effective amount of tissue factor protein mutant to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Typically, the clinician will administer the tissue factor protein mutant until a dosage is reached that achieves the desired effect. The progress of this therapy is easily monitored by conventional assays.

In addition to being useful for treatment of myocardial infarction and septic shock, the tissue factor protein mutant of this invention may be useful for treating other disease states in which DIC may arise including but not limited to cardiac arrest, extensive trauma, bites of poisonous snakes, acute liver disease, major surgery, burns, septic abortion, heat stroke, disseminated malignancy, pancreatic and ovarian carcinoma, promyelocytic leukemia, myocardial infarction, neoplasms, systemic lupus erythematosus, renal disease and eclampsia, as well as those etiologic factors and disorders set forth in Braunwald, E. (ed), et al., *Harrisons Principles of Internal Medicine,* 11th ed, McGraw Hill, page 1478.

All references cited in this specification are expressly incorporated by reference.

The following examples are offered by way of illustration and not by way of limitation.

EXAMPLE 1

1. Preparation of Tissue Factor cDNA

The full length tissue factor cDNA (1347 bases) was obtained as described by Fisher et al., (*Thromb. Res.,* 48:98 [1987]). This cDNA was inserted into the vector pSP64 (Promega, catalog no. P1091) between the Hind III and Sal I sites, using standard digestion and ligation procedures, to generate the plasma pSP64TFHS. This plasmid was used as a source of tissue factor cDNA for making the tissue factor mutants.

2. Generation of the Tissue Factor Mutant K165A, K166A

A 1358 base fragment from pSP64TFHS containing the full-length tissue factor amino acid coding sequence was obtained by restriction endonuclease digestion of 1 μg of plasmid DNA to completion with 1 unit each of the restriction enzymes Hind III and Sst I (Bethesda Research Laboratories [BRL] Bethesda, Md.) in a 20 μl reaction mixture containing 50 mM Tris HCl, pH 7.4, 10 mM $MgCl_2$, 50 mM NaCl, at 37° C. for 1 hour. The reaction mixture was then electrophoresed on a 1% agarose gel along with molecular size markers (purchased from BRL) in Tris-acetate-EDTA buffer containing ethidium bromide (as described in sections 6.3–6.15 of Sambrook et al., *Molecular Cloning: A Laboratory Manual*, Cold Spring Harbor Laboratory Press, Cold Spring Harbor, N.Y., [1989]). The agarose fragment containing the 1358 base tissue factor cDNA fragment (visualized using 300 nm ultra-violet light) was cut out and the DNA was electroeluted from the gel (as described in section 6.28–6.29 of Sambrook et. al.supra.).

The 1358 base cDNA fragment was inserted into the phagemid vector pSelect™ (Promega Corporation catalog no. Q6301) to generate the plasmid pSelectTF. Construction of pSelectTF was by ligation of the 1358 base TF cDNA bearing Hind III and Sst I cohesive termini into pSelect™ previously cut with the restriction endonucleases Hind III and Sst I. This was done by mixing the electroeluted TF cDNA fragment with 0.2 μg of digested pSelect™ DNA in a reaction mixture containing 50 mM Tris HCl, pH 7.6, 10 mM MgCl$_2$, 1 mM ATP, 1 mM dithiothreitol and 1 unit of T4 DNA ligase (BRL) and incubating the mixture at 14° C. for 14 hours. The ligated DNA was transformed into an *Escherichia coli* lac$^-$ strain equivalent to JM 109, and putative recombinants were selected based on tetracycline resistance and inability to produce blue colored colonies on indicator plates containing X-gal (5-bromo-4-chloro-3-indolyl β-D-galactopyranoside) and IPTG (isopropyl β-D-thiogalactopyranoside), using standard procedures well known in the art. Confirmation of successful cloning was done by isolating plasmid DNA from putative recombinants using the DNA miniprep procedure (sections 1.29–1.30 of Sambrook et. al., supra) and digesting 0.5 μg of each plasmid isolated with 1 unit of the restriction enzyme Eco RI (BRL) in a 10 μl reaction mixture, using the buffer ("React 4") supplied with the enzyme by the manufacturer. Correctly ligated DNAs produced an 863 base fragment after digestion as seen by electrophoresis in 1% agarose by comparison with simultaneously electrophoresed molecular size markers. One such correctly ligated DNA (pSelectTF) was used for mutagenesis.

3. Mutagenesis of Tissue Factor cDNA

Mutagenesis was conducted using in the Altered Sites™ in vitro Mutagenesis System kit (Promega catalog no. Q6210). An oligonucleotide was prepared (using standard synthesis procedures) and was used for guiding the mutagenesis. The sequence of this oligonucleotide was 5'-TCAAGTTCAGGAGCGGCAACAGCCAAAACA-3' (SEQ ID NO: 2) and it hybridizes to bases 676–706 of the wild type tissue factor cDNA. This oligonucleotide codes for Ala at amino acid positions 165 and 166. The Altered Sites™ Mutagenesis System kit protocol consists of standard procedures well known in the art, performed essentially as follows: single stranded DNA template was produced by infecting an *E. coli* JM 109 cell culture containing the phagemid pSelect TF with helper phage (M13K07, commercially available) at a multiplicity of infection of about 10 (i.e. 10 helper phage particles per cell). This culture was incubated on a shaker at 37° C. for about 6–10 hours. The culture supernatant was then collected by pelleting the cells at 12,000×g for 15 minutes, and repeating, to completely clear the supernatant of debris. The phage particles, contained in the supernatant, were precipitated by adding 0.25 volume of phage precipitation solution (3.75M NH$_4$OAc, pH 7.5, 20% polyethylene glycol [m.w. 8,000]), leaving on ice for 30 min., and then centrifuging for 15 min. at 12,000×g. The pellet, containing the phage particles, was resuspended in 400 μl TE (10 mM Tris-HCl pH 8, 1 mM EDTA) buffer. Four-hundred microliters of chloroform:isoamylalcohol (24:1) was then added to lyse the phage. The solution was vortexed and centrifuged at 12,000×g for 5 minutes. The phagemid DNA, contained in the upper, aqueous phase, was then collected and phenol extracted with a solution of TE saturated phenol:chloroform (1 part phenol saturated with TE into 1 part chloroform solution [24:1 chloroform:isoamyl alcohol]). The phenol:chloroform extraction was repeated, and the DNA was precipitated by adding 0.5 volume of 0.75M NH$_4$OAc in 2 volumes of ethanol. This solution was kept at −20° C. for 30 min., after which time it was centrifuged at 12,000×g for 5 minutes. The supernatant was removed and the pellet was rinsed in 70% ethanol and re-centrifuged at 12,000×g for 2 minutes. The pellet was then dried under vacuum and resuspended in 20 μl water.

After single stranded template had been prepared, the tissue factor cDNA mutant was generated from this template essentially according to the Promega Altered Sites™ protocol:

The oligonucleotide described above, containing the mutation coding for Ala at amino acid positions 165 and 166 (1.25 pmol), was combined with 2 μl annealing buffer (provided with the Promega Altered Sites™ kit), 0.05 pmol of the single stranded phagemid template, and 0.25 pmol of the ampicillin repair oligonucleotide provided with the Altered Sites™ kit (the pSelect phagemid is not amp$^R$; use of this oligonucleotide generates amp resistance in the mutants, thus creating a simple means—amp resistance—to select mutants). This solution was heated to 70° C. for 5 min. and cooled slowly to room temperature. To the cooled solution was added 3 μl of synthesis buffer (provided with the Promega Altered Sites™ kit), 1 μl of T4 DNA polymerase (10 U/μl), 1 μl of T4 DNA ligase (2 U/μl) and 5 μl water. This mixture was incubated at 37° C. for 90 minutes.

After incubation, the entire reaction mixture was added to 200 μl of competent *E. coli* strain BMH 71-18 mutS (provided with the Promega Altered Sites™ kit) containing 3 μl of dimethylsulfoxide (DMSO). The solution was placed on ice for 30 minutes. Four ml of LB broth (LB broth per liter: 10 g Bactotrypone, tryotone, 5 g Bacto-yeast extract and 5 g NaCl, pH 7.5) was then added and the cells were incubated at 37° C. for one hour to allow the cells to recover. Ampicillin was then added to a final concentration of 125 μg/ml and the culture was kept shaking at 37° C. for about 12 hours.

Mutated phagemid DNA was then extracted from the cells using the standard mini-prep procedure (sections 1.74–1.84 of Sambrook et al., supra.) and the DNA was transformed into JM 109 *E. coli* cells. Single colonies were screened for the presence of the tissue factor mutant by hybridization with the mutagenizing oligonucleotide under standard conditions as described in sections 1.90–1.104 of Sambrook et al., supra, and washing at a stringency of about 2×SSC at 60° C. for 30 minutes.

4. Cloning of Mutagenized Tissue Factor cDNA into Expression Vector pRK5

The mutagenized tissue factor cDNA cloned in pSelect™ was excised by a Hind III-Sal I double digestion as follows: phagemid DNA (1 μg) was first digested with 1 unit of Hind III in a 10 μl reaction mixture containing 50 mM Tris HCl, pH 8, 10 mM MgCl$_2$, 50 mM NaCl at 37° C. for 1 hour. To this digest was added 4 μl of a solution of 375 mM Tris HCl pH 7.6, 25 mM MgCl$_2$, 625 mM NaCl in addition to 5 μl of water and 1 unit of Sal I restriction enzyme, and the digestion was continued for 1 hour at 37° C. A 1358 base tissue factor cDNA fragment bearing Hind III and Sal I cohesive ends was isolated after agarose gel electrophoresis.

The expression vector pRK5 (0.2 µg) was similarly digested with Hind III and Sal I and the mutated tissue factor cDNA was ligated to it using the ligation procedure described above. Transformation of the ligated DNA into *E. coli* strain 294 was done as described in sections 1.74–1.84 of Sambrook et. al., supra, selecting for carbenicillin resistance.

Putative recombinants were screened for successful mutagenesis by DNA sequencing. The sequencing was conducted using reagents and protocols supplied by United States Biochemicals, Cleveland, Ohio, in their Sequenase® version 2.0 DNA sequencing kit. The oligonucleotide used to prime the sequencing reactions had the sequence 5'-CAA-CACTTTCCTAAGCC-3'(SEQ ID NO: 3) Alternatively, other oligonucleotides that hybridize about 100 bases upstream or downstream from the region of the DNA to be sequenced could be used.

The plasmid containing the tissue factor mutant K165A, K166A was identified from sequencing analysis and named pRK5TFAA.

5. Expression of pRK5TFAA

The plasmid pRK5TFAA was transfected into human kidney 293 cells (grown in monolayer culture in a 50:50 mixture of Eagle's medium [low glucose DMEM] and Ham's F12 medium using the calcium phosphate precipitation method (Graham F., et al., *Virology*, 52:456 [1973]). Cells expressing the tissue factor mutant were lysed using 1% Triton X-100 in TBS buffer (10 mM Tris HCl, 137 mM NaCl, pH 7.4). Dilutions of the lysates were assayed by ELISA using rabbit and goat polyclonal antibodies raised against tissue factor protein to quantitate mutant tissue factor expression levels.

6. Binding of Factor VII to Tissue Factor Mutant and Inhibition of Wild-Type Tissue Factor Activity.

Human embryonic kidney 293 cells, transfected to express either the wild-type tissue factor protein or the K165A, K166A mutant, were washed once with Buffer A (10 mM Hepes, 137 mM NaCl, 4 mM KCl, 11 mM glucose, pH 7.4) containing 10 mM EDTA and then three times with Buffer A. Transfected and mock transfected cells (mock transfected cells are those transfected with pRK5 vector that did not contain the tissue factor cDNA insert) were then incubated with 50 nM $^{125}$-I labelled factor VII (labelling with $^{125}$-I was accomplished using the Iodo-Gen™ iodination reagent purchased from Pierce (catalog no. 28600) essentially following the protocol supplied by the manufacturer) in incubation buffer (Buffer A containing 5 mM CaCl$_2$ and 0.5% BSA). After incubating for 1 hour at room temperature, unbound factor VII/VIIa was removed by three washes with buffer A containing 5 mM CaCl$_2$. Bound factor VII/VIIa was then eluted from the cells by incubating for 5 min in Buffer A containing 10 mM EDTA. The SDS polyacrylamide gel shown in the upper panel of FIG. 5 indicates the results. Lane 1 is $^{125}$-I purified labelled factor VII; lane 2 is $^{125}$-I-factor VII/VII$_a$ eluted off cells transfected with wild type TF; lane 3 is $^{125}$-I factor VII/VII$_a$ eluted off cells transfected with the K165A, K166A TF mutant; and lane 4 is $^{125}$-I factor VII/VIIa eluted off mock transfected cells (nothing seen, indicating that factor VII/VIIa did not bind to mock transfected cells). The samples were reduced with DTT to show cleavage of bound factor VII. The positions of the molecular weight standards are indicated. The dried gel was autoradiographed. Lower panel: The activity of wild-type TF in a chromogenic assay (O'Brien et al., supra) was used as a reporter of apparent factor VII concentration in the presence of increasing concentrations of mutant TF ('ala-ala'). Relipidation mixtures containing 0.001 picomoles/200 µl incubation of wild type TF and varying amounts of mutant K165A, K166A TF were assayed for activity using a limiting concentration of factor VII (0.1 picomole/200 µl incubation). The values for 'apparent [factor VII]' were derived from a standard curve of activity of 0.001 picomole of TF in varying concentrations of factor VII.

EXAMPLE 2

Coronary Artery Thrombosis and Treatment with Tissue Factor Protein Mutant

Mongrel dogs weighing approximately 20–25 kg are anesthetized with a slow intravenous injection of sodium phenobarbital, incubated and placed on an artificial ventilator. A left thoracotomy is performed in the 5th–6th intercostal space, and an arterial catheter is placed in the internal mammary artery for blood pressure monitoring. Procainamide (1.5 g injected intramuscularly in 2–3 sites) is then provided, the pericardium is opened, and a pericardial cradle is prepared. The left anterior descending coronary artery is dissected out from the epicardium, side branches are ligated, and a 2.5 cm segment is isolated. An electromagnetic flow probe (Carolina Medical Electronics FM501, King, N.C.) is placed on the most proximal portion of the segment and intravenous lidocaine (15 mg bolus followed by a constant infusion at 1 mg/min) is infused. A control left coronary anglogram is performed by injecting approximately 2 ml of Renografiin 76, by hand, through a modified Judkin's 7 French catheter inserted from a carotid artery. 1 ml of blood is then removed and kept in a sydnge for later use in forming the thrombus, and heparin (5000 U intravenous bolus) is administered. Additional 1000 U boluses of heparin are administered at hourly intervals. A permanent 2 mm wide constrictor is placed near the distal end of the segment and adjusted so as to reduce coronary artery blood flow to approximately 40±10% of control.

High resolution post-mortem anglograms in selected animals show that a constriction, so placed, decreases the luminal diameter by more than 90%. The 1 cm of coronary artery just proximal to the constriction is then emptied of blood and isolated between temporary silk snares. Intimal damage is induced by grasping the segment with forceps, and then the segment is flushed by releasing the proximal snare and injection of saline retrograde through a cannulated side branch. The segment is then reisolated and 0.2 ml of thrombin (Parke-Davis topical thrombin, 1000 U/ml, Morris Plains, N.J.) is introduced. 0.1 ml of the stored blood is injected into this isolated segment. After approximately 5 minutes, first the proximal and then the distal ties are released and the side branch catheter is removed. During this procedure, the permanent constrictor remains in place.

Approximately 30 minutes after injecting the thrombin and blood, and after a repeated anglogram confirms the presence of a complete coronary artery occlusion, slow intravenous injections of tissue factor protein mutant K165A, K166A, acetylsalicylic acid (35 mg/kg) or dipyridamole (0.6 mg/kg) are administered. Approximately 10 minutes later, a 30-minute infusion of rt-PA (15 mg/kg/min for the two chain form or 30 mg/kg/min for the single chain form) is initiated.

If partial coronary artery reperfusion does not occur within the 30-minute infusion period, rt-PA infusion is continued for an additional 30 minutes. The blood flow in the affected vessel is monitored continuously. An anglogram is immediately performed after restoration of blood flow.

The reperfusion time is taken as the number of minutes from the beginning of the rt-PA infusion until reperfusion is documented by the flow meter and is confirmed by the repeat anglogram showing complete antegrade filling of the artery with rapid clearance of the dye (less than 4 cardiac cycles). After reperfusion is obtained, blood flow is monitored for evidence of reocclusion, with a final confirmation again being obtained by angiography, using the same criteria as are used for establishing reperfusion. The reocclusion time is taken as the interval between documented reperfusion and reocclusion. The above described animal model closely simulates the response to thrombolytic therapy by human patients having acute myocardial infarction.

Bleeding times are performed before and 30 min after injections of the tissue factor protein mutant K165A, K166A with a spring—loaded blade device (Simplate, General Diagnostic, Morris Plains, N.J. or Surgicutt Int. Technidyne Corp., Edison, N.J.), applied to a shaved foreleg. Venous blood samples for determination of the levels of fibrinogen, activated partial thromboplastin time, ADP—induced platelet aggregation and $^{125}$I-7E3 binding are collected into 0.01M citrate containing 150 KIU/ml aprotinin. (Sigma, St. Louis, Mo.) Platelet counts are performed on blood drawn into EDTA using an automated particle counter (Coulter, Hialeah, Fla).

We claim:

1. An isolated substantially purified nucleic acid molecule encoding a tissue factor protein mutant molecule wherein either or both of the positively charged amino acid residues 165 and 166 are substituted with an α-amino acid other than one bearing a substantially positively charged sidechain at physiological pH.

2. The nucleic acid molecule of claim 1 that is DNA and has the translated amino acid sequence shown in FIG. 1 (SEQ ID NO: 1).

3. The nucleic acid molecule of claim 1 further comprising a promoter operably linked to the nucleic acid molecule.

4. An expression vector comprising the nucleic acid molecule of claim 1 operably linked to control sequences recognized by a host cell transformed with the vector.

5. A host cell transformed with the vector of claim 4.

6. A process of using the nucleic acid molecule of claim 1 comprising: expressing the tissue factor protein mutant in a cultured host cell transformed with a vector comprising the nucleic acid molecule encoding the tissue factor protein mutant operably linked to control sequences recognized by the host cell transformed with the vector and recovering the tissue factor protein mutant from the host cell.

7. The process of claim 6 wherein the tissue factor protein mutant is recovered from the host cell culture medium.

8. The nucleic acid molecule of claim 1 wherein the tissue factor protein mutant is selected from the group: mature human tissue factor protein, human tissue factor protein with amino acid residues from about 243 to 263 deleted, and human tissue factor protein with amino acid residues from about 220 to 263 deleted.

9. The nucleic acid molecule of claim 8 wherein both positively charged amino acid residues 165 and 166 are substituted with an α-amino acid other than one bearing a positively charged sidechain at physiological pH.

10. The nucleic acid molecule of claim 8 wherein either or both positively charged amino acid residues 165 and 166 are substituted with glutamic acid or aspartic acid.

11. The nucleic acid molecule of claim 9 wherein the α-amino acid is other than lysine or arginine.

12. The nucleic acid molecule of claim 9 wherein the α-amino acid is selected from amino acids bearing an uncharged sidechain.

13. The nucleic acid molecule of claim 12 wherein the α-amino acid is alanine.

14. The nucleic acid molecule of claim 13 wherein amino acid residues from about 243 to 263 are deleted.

15. The nucleic acid molecule of claim 13 wherein amino acid residues from about 220 to 263 are deleted.

16. An isolated substantially purified nucleic acid molecule comprising the nucleic acid molecule of claim 1 fused to a nucleic acid molecule encoding a heterologous polypeptide.

\* \* \* \* \*